(12) United States Patent
Hargreaves et al.

(10) Patent No.: US 9,029,342 B2
(45) Date of Patent: May 12, 2015

(54) COMPOSITIONS OF MATTER THAT REDUCE PAIN, SHOCK, AND INFLAMMATION BY BLOCKING LINOLEIC ACID METABOLITES AND USES THEREOF

(71) Applicant: Board of Regents of the University of Texas System, Austin, TX (US)

(72) Inventors: Kenneth Michael Hargreaves, San Antonio, TX (US); John Gordon Bruno, Boerne, TX (US)

(73) Assignees: Board of Regents of the University of Texas System, Austin, TX (US); OTC Technologies, LLC, San Antonio, TX (US)

( * ) Notice: Subject to any disclaimer, the term of this patent is extended or adjusted under 35 U.S.C. 154(b) by 0 days.

(21) Appl. No.: 14/029,440

(22) Filed: Sep. 17, 2013

(65) Prior Publication Data

US 2014/0128588 A1    May 8, 2014

Related U.S. Application Data

(60) Provisional application No. 61/702,232, filed on Sep. 17, 2012.

(51) Int. Cl.
*C12N 15/115* (2010.01)
*A61K 47/48* (2006.01)

(52) U.S. Cl.
CPC ........ *C12N 15/115* (2013.01); *A61K 47/48092* (2013.01); *C12N 2310/16* (2013.01); *C12N 2310/351* (2013.01); *C12N 2310/3519* (2013.01)

(58) Field of Classification Search
USPC ........ 435/9, 91.1, 455; 514/1, 2, 44; 536/23.1
See application file for complete search history.

*Primary Examiner* — Jane Zara
(74) *Attorney, Agent, or Firm* — Meyertons, Hood, Kivlin, Kowert & Goetzel, P.C.; Eric B. Meyertons

(57) ABSTRACT

A method for treating and/or diagnosing pain and the source or type of pain, shock, and/or inflammatory conditions in a subject. A method of using a therapeutically effective amount of a DNA or RNA aptamer that shows high affinity for OLAMs to at least partially treat pain, shock, and/or inflammatory conditions in a subject. The DNA or RNA aptamer that shows high affinity for OLAMs may be coupled to a plasma protein binding compound or a pharmacologically active agent. A method of treating and or diagnosing pain, shock, and/or inflammatory conditions in a subject may include inactivating or preventing at least one linoleic acid metabolite to treat certain conditions (e.g., pain, shock, and/or inflammation) using a DNA or RNA aptamer that shows high affinity for OLAMs.

22 Claims, 2 Drawing Sheets

COMPOSITIONS OF MATTER THAT REDUCE PAIN, SHOCK, AND INFLAMMATION BY BLOCKING LINOLEIC ACID METABOLITES AND USES THEREOF

PRIORITY CLAIM

This application claims the benefit of U.S. Provisional Application No. 61/702,232 filed on Sep. 17, 2012.

BACKGROUND OF THE INVENTION

1. Field of the Invention

The present invention generally relates to the fields of treating or diagnosing pain, shock, and/or inflammatory conditions in a subject. More specifically, the present invention is related to the use of a pharmaceutical composition that comprises one or more DNA or RNA ligands or aptamers that inhibit and/or minimize the production of oxidized linoleic acid metabolites and/or block the activity of oxidized linoleic acid metabolites.

2. Description of the Relevant Art

Many pain conditions are poorly managed by currently available analgesics. For example, burn injuries affect more than two million people annually in the United States alone. Importantly, poor pain control in burn patients is known to increase the risk for long term adverse outcomes. This is a critical issue since surveys indicate that about one-half of burned patients have inadequate pain management. Patients suffering from a burn injury experience pain at the initial heat insult, during healing, and even in a chronic form, post burn injury.

Currently available analgesics for treating burn pain (e.g., opiates, local anesthetics) demonstrate only limited efficacy and are associated with considerable adverse effects. In addition to burn pain, there are many other pain states (e.g., inflammatory pain, neuropathic pain, cancer pain, herpes zoster pain, etc) for which currently available analgesics exhibit very limited activity, especially with repeated dosing.

Shock resulting from massive trauma, severe blood or fluid loss, systemic infections, insufficient cardiac output, or any other disorder or injury that leads to a hypoperfusional state is a serious, life threatening condition. Even with aggressive and prompt treatment shock is often fatal.

Many clinical pain conditions are classified as "idiopathic" since the mechanism is not known. Development of a diagnostic test that indicates which drugs might relieve the pain would have great benefit in treating patients.

It is therefore desirable to develop a safer method of treating a pain, shock, and/or inflammatory condition in a subject.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
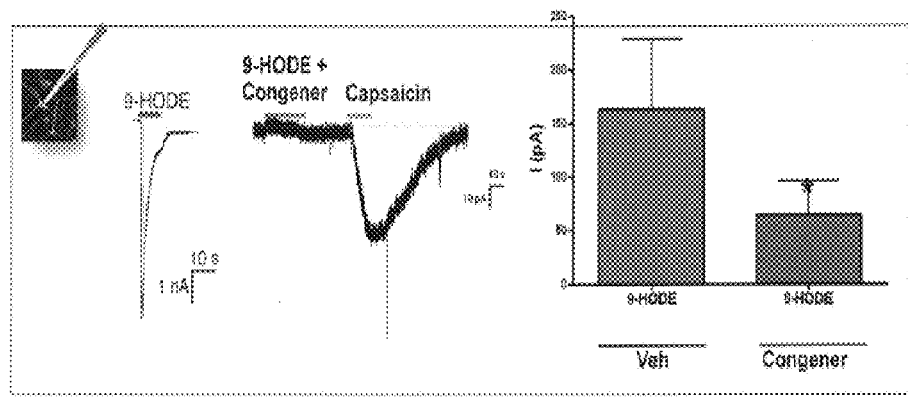
FIG. 1 depicts data that indicates that pre-treatment with SEQ ID NO. 84 (anti-9-HODE aptamer) blocks activation of cultured capsaicin-sensitive neurons using patch clamp electrophysiology.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

SUMMARY

In some embodiments, one or more compounds that inhibit and/or minimize the production of oxidized linoleic acid metabolites and/or block the activity of oxidized linoleic acid metabolites may be used in the preparation of a pharmaceutical composition for treating pain, shock, inflammatory conditions, or combinations thereof, in a mammal in need thereof.

A pharmaceutical composition for treating pain, shock, inflammatory conditions, or combinations thereof in a subject may include one or more compounds that inhibit and/or minimize the production of oxidized linoleic acid metabolites and/or block the activity of oxidized linoleic acid metabolites and one or more pharmaceutically acceptable carriers.

In some embodiments, the pharmaceutical composition comprises one or more DNA or RNA aptamers or segments of aptamers (binding sites) that block the activity of oxidized linoleic acid metabolites. Aptamers that may be used in the pharmaceutical composition include aptamers that bind to a hydroxy linoleic acid metabolite, aptamers that bind to an epoxy linoleic acid metabolite, and aptamers that bind to an oxo linoleic acid metabolite. Examples of linoleic acid metabolites that the aptamer binds to include, but are not limited to: (10E,12Z)-9-oxooctadeca-10,12-dienoic acid; (9Z,11E)-13-oxooctadeca-9,11-dienoic acid; 9-hydroxyoctadecadienoic acid; 13-hydroxyoctadecadienoic acid; 9(10)-dihydroxy-octadec-12-enoic acid; 12,13-dihydroxy-9Z-octadecenoic acid; (12Z)-9,10-epoxyoctadecenoic acid; 12,13-epoxyoctadec-9Z-enoic acid, 12,13-dihydroxyoctadec-9-enoic acid, (12R,13S)-(9Z)-12,13-epoxyoctadecenoic acid, 9,10-dihydroxyoctadec-9-enoic acid and (9R,19S)-(9Z)-9,10-epoxyoctadecenoic acid.

In an embodiment, the pharmaceutical composition may include one or more DNA or RNA aptamers or segments of aptamers (binding sites) that inhibit and/or minimize the production of oxidized linoleic acid metabolites. In one embodiment, at least one of the compounds that inhibits and/or minimizes the production of oxidized linoleic acid metabolites is a DNA or RNA aptamer that binds to cytochrome P-450 enzyme.

In an embodiment, a method of treating pain, shock, inflammatory conditions, or combinations thereof in a subject includes administering to a subject who would benefit from such treatment a therapeutically effective amount of a pharmaceutical composition, wherein the pharmaceutical composition comprises one or more DNA or RNA aptamers that inhibit and/or minimize the production of oxidized linoleic acid metabolites and/or block the activity of oxidized linoleic acid metabolites. The pharmaceutical composition may be administered intravenously, by inhalation, orally, topically, subcutaneously or directly into the central or peripheral nervous system.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DEFINITIONS

The terms used throughout this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered by parenteral, subcutaneous, intravenous, intra-articular, intracoronary, rectal, intramuscular, inhalational, intra-nasal, intra-peritoneal, transdermal, direct application to a wounded site, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, the term "agonist" generally refers to a type of ligand or drug that binds and alters the activity of a receptor.

As used herein, the term "antagonist" generally refers to a type of receptor ligand which binds a receptor but which does not alter the activity of the receptor; however when used with an agonist, prevents the binding of the agonist to the receptor hence the effect of the agonist.

As used herein, the term "allodynia" generally refers to pain from stimuli which are not normally painful. The pain may occur other than in the area stimulated. As used herein, the term "hyperalgesia" generally refers to increased pain perception from stimuli which are normally painful. Hyperalgesia may occur other than in the area stimulated. Since many clinical pain conditions are characterized by both allodynia and hyperalgesia, the use of either term in this application is meant to include both pain conditions.

As used herein, the term "antinociception" generally refers to a reduction in pain sensitivity.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release" or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, pharmaceutical compositions, formulations and preparations may include pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the term "pharmaceutically acceptable salts" includes salts prepared by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, pyrimidines, theobromine, triethylamine, trimethylamine, tripropylamine, tromethamine, etc.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

As used herein the term "subject" generally refers to a mammal, and in particular to a human.

As used herein, the term "treat" generally refers to an action taken by a caregiver that involves substantially inhibiting, slowing or reversing the progression of a disease, disorder or condition, substantially ameliorating clinical symptoms of a disease disorder or condition, or substantially preventing the appearance of clinical symptoms of a disease, disorder or condition.

Terms such as "in need of treatment," "in need thereof," "benefit from such treatment," and the like, when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

By "therapeutically effective amount" is meant an amount of a drug or pharmaceutical composition that will elicit at least one desired biological or physiological response of a cell, a tissue, a system, animal or human that is being sought by a researcher, veterinarian, physician or other caregiver.

Methods and Compositions

Mechanistically, burn injury is a unique type of tissue damage where transient exposure to heat results in long lasting changes in the exposed tissue (e.g., skin). The studies performed in humans and in animals demonstrated that these changes in the damaged tissue are at least in part responsible for the development and maintenance of ongoing pain or hyperalgesia. The heat injured tissue generates various inflammatory mediators that sensitize ion channels such as transient receptor potential vanilloid 1 or TRPV1 to evoke ongoing pain and hyperalgesia. Other important pain conditions include inflammatory, neuropathic, cancer and the like.

TRPV1, also known as the capsaicin receptor, plays a pivotal role in burn injury and other important pain conditions by evoked hyperalgesia and allodynia such that the mice deficient in TRPV1 protein show little to no hyperalgesia in these models. The key role played by TRPV1 in the development of thermal hyperalgesia and possibly mechanical hyperalgesia in various pain models is well established in animal and human studies. Signaling cascades initiated by a variety of inflammatory mediators may sensitize TRPV 1 and contribute to inflammatory hyperalgesia. Given the importance of TRPV1 in inflammatory pain, burn pain and cancer pain, including other various pain states, antagonists against TRPV 1 may be used for treating pain and/or inflammatory conditions. However, recent studies have demonstrated some serious on target side effects of TRPV 1 antagonists that may exclude their clinical use. These data necessitate additional research in findings ways to block TRPV1 activation without using the antagonists.

A variety of endogenous molecules have been shown to activate TRPV 1 and they include anandamide, N-arachidonoyl-dopamine, N-oleoyldopamine, polyamines etc. Such endogenous TRPV1 ligands may be generated during inflammation and contribute to constitutive activation of TRPV1. Barring a few reports, the role of these endogenous TRPV1 ligands in physiological or pathological pain is not known. Interestingly, TRPV1 may be activated by stimuli such as protons and noxious heat. The mechanism by which heat activates TRPV1 is not completely understood although several hypotheses have been proposed. Heat, cancer cells and the process of inflammation or nerve injury may generate endogenous TRPV1-stimulating ligands in the injured tissue and thus initiate a noxious pain sensation. In such tissues, the endogenous TRPV1 ligands may be constitutively synthesized for longer durations and activate TRPV1 to produce ongoing pain sensation in the absence of heat. A similar pathway may exist for inflammatory or other pain conditions as well.

In some embodiments, injury to tissues including but not limited to skin results in generation of oxidized linoleic acid metabolites. These metabolites represent a novel family of endogenous TRPV1 ligands. These ligands activate TRPV1 expressed by sensory nerve terminals in the damaged tissue. The opening of TRPV1 leads to generation of action potentials and the pain sensation in the somatosensory cortex.

In some embodiments, metabolites of linoleic acid have been identified as TRPV1 agonists. Linoleic acid is also known by its IUPAC name cis, cis-9,12-octadecadienoic acid. Linoleic acid has a structure:

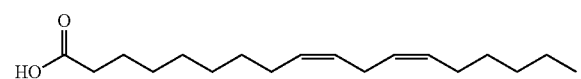

In some embodiments, pharmacological interventions that can block the generation of the endogenous TRPV1 ligand in response to heat may be of therapeutic use. In addition, the measurement of linoleic acid metabolites may constitute a novel method for diagnosing pain or shock conditions, thereby guiding treatment selection. For example, we have found that levels of linoleic acid metabolites may be correlated to the level of pain or discomfort experienced by the patient. The level of pain before and after treatment may therefore be assessed by measuring the level of one or more linoleic acid metabolites.

In some embodiments, oxidized linoleic acid metabolites are generated upon heat stimulation of skin. Oxidized linoleic acid metabolites ("OLAMs") include, but are not limited to, oxo linoleic acid metabolites, hydroxyl linoleic acid metabolites, and epoxy linoleic acid metabolites. Examples of oxo linoleic acid metabolites include, but are not limited to (10E, 12Z)-9-oxooctadeca-10,12-dienoic acid (9-oxoODE, 9-KODE) and (9Z,11E)-13-oxooctadeca-9,11-dienoic acid (13-oxoODE, 13-KODE). Examples of hydroxyl linoleic acid metabolite include, but are not limited to: 9-hydroxyoctadecadienoic acid (9-HODE); β-hydroxyoctadecadienoic acid (13-HODE); 9(10)-dihydroxy-octadec-12-enoic acid (9,10-DiHOME); and 12,13-dihydroxy-9Z-octadecenoic acid (12,13-DiHOME). Examples of epoxy linoleic acid metabolites include, but are not limited to: (12Z)-9,10-epoxyoctadecenoic acid (9(10)-EpOME) and 12,13-epoxyoctadec-9Z-enoic acid (12(13)-EpOME). It is believed that oxidized linoleic acid metabolites may function as endogenous agonists to TRPV1 and other receptors.

In some embodiments, the blockade of synthesis or immunoneutralization of oxidized linoleic acid metabolites results in decreased activation of pain sensing neurons by heat in vitro and results in thermal antinociception in vivo. Neutralization of oxidized linoleic acid metabolites may be accomplished by the use of one or more aptamers that bind to at least one oxidized linoleic acid metabolite.

Aptamers were selected on their basis of binding to OLAMs. More specifically, a screen of randomly synthesized aptamers was made for high affinity binding to 9-hydroxyoctadecadienoic acid (9-HODE) and 13-hydroxyoctadecadienoic acid (13-HODE). See list of aptamers below identified with 9-HODE and 13-HODE recognizing properties. The aptamers discovered exhibiting the highest binding affinity have the following sequences: for the OLAM 9-HODE, the aptamer with the following sequence: 5'-ATA CGG GAG CCA ACA CCA CCG AAT GTG CTG CAG GAC TAA TCT GGA TGG CCA TGC AGA GCA GGT GTG ACG GAT-3' (SEQ ID NO. 84); and for the OLAM 13-HODE, the aptamer with the following sequence: 5'-ATC CGT CAC ACC TGC TCT GGG GGG GGA AGC TCG TGG TAT AAG GGG CGT TGA GGT GGT GTT GGC TCC CGT AT-3' (SEQ ID NO. 67).

In some embodiments, aptamers that show high affinity for two or more different OLAMs may be linked together. A protein, ester or other type of linkage may be formed between two aptamers (for example the 9-HODE aptamer and the 13-HODE aptamer) or DNA sequences to provide improved pain relief as well as improved pharmacokinetics due to slowed clearance by the kidneys and major organs and reduced exonuclease activity against DNA or RNA aptamer compositions in serum or other body fluids.

| Clone Name | SEQ ID NO. | DNA Aptamer Sequence |
|---|---|---|
| CYP-1F | 1 | ATA CGG GAG CCA ACA CCA TCA TGC TAC TAC CGG GCC CTT TCA TCC TAA GCA CGG AGA GCA GGT GTG ACG GAT |
| CYP-1R | 2 | ATC CGT CAC ACC TGC TCT CCG TGC TTA GGA TGA AAG GGC CCG GTA GTA GCA TGA TGG TGT TGG CTC CCG TAT |
| CYP-2/9b/25F | 3 | ATA CGG GAG CCA ACA CCA TCC AAT GAG GCC ATG GAC CGG TAA ACT CGG ACG CGC AGA GCA GGT GTG ACG GAT |
| CYP-2/9b/25R | 4 | ATC CGT CAC ACC TGC TCT GCG CGT CCG AGT TTA CCG GTC CAT GGC CTC ATT GGA TGG TGT TGG CTC CCG TAT |
| CYP-3/1-0/20/24bF | 5 | ATA CGG GAG CCA ACA CCA GTC CGT TAT GAC ATG TCC GGA CCC GTA CGC GTG TCA AGA GCA GGT GTG ACG GAT |
| CYP-3/1-0/20/24bR | 6 | ATC CGT CAC ACC TGC TCT TGA CAC GCG TAC GGG TCC GGA CAT GTC ATA ACG GAC TGG TGT TGG CTC CCG TAT |
| CYP-4F | 7 | ATA CGG GAG CCA ACA CCA TGC CCG CTG TAG TGG TCT CTT AAC TTA CCC TCG TGC AGA GCA GGT GTG ACG GAT |
| CYP-4R | 8 | ATC CGT CAC ACC TGC TCT GCA CGA GGG TAA GTT AAG AGA CCA CTA CAG CGG GCA TGG TGT TGG CTC CCG TAT |
| CYP-5F | 9 | ATA CGG GAG CCA ACA CCA CCC CCC CAT ACT CTT ATT TGC GAC CTC TTT CGC TAC AGA GCA GGT GTG ACG GAT |
| CYP-5R | 10 | ATC CGT CAC ACC TGC TCT GTA GCG AAA GAG GTC GCA AAT AAG AGT ATG GGG GGG TGG TGT TGG CTC CCG TAT |
| CYP-6F | 11 | ATA CGG GAG CCA ACA CCA TCT CAC CCA TGC CCA CAA CCA GTC CAC GCT ACG CCG AGA GCA GGT GTG ACG GAT |
| CYP-6R | 12 | ATC CGT CAC ACC TGC TCT CGG CGT AGC GTG GAC TGG TTG TGG GCA TGG GTG AGA TGG TGT TGG CTC CCG TAT |
| CYP-7aF | 13 | ATA CGG GAG CCA ACA CCA CTT CAT TAA GTG GTA TTT TGG GCA GGA GAG CAT CAC AGA GCA GGT GTG ACG GAT |
| CYP-7aR | 14 | ATC CGT CAC ACC TGC TCT GTG ATG CTC TCC TGC CCA AAA TAC CAC TTA ATG AAG TGG TGT TGG CTC CCG TAT |
| CYP-7bF | 15 | ATA CGG GAG CCA ACA CCA CCA GGA TAC AAC CCC ACC ATA GAC TAT TCA CTG ATA GAG CAG GTG TGA CGG AT |
| CYP-7bR | 16 | ATC CGT CAC ACC TGC TCT ATC AGT GAA TAG TCT ATG GTG GGG TTG TAT CCT GGT GGT GTT GGC TCC CGT AT |
| CYP-8F | 17 | ATA CGG GAG CCA ACA CCA AGG CGC GCA TTA ATT TAA TGA CAG AGA TCA CGA ATC AGA GCA GGT GTG ACG GAT |
| CYP-8R | 18 | ATC CGT CAC ACC TGC TCT GAT TCG TGA TCT CTG TCA TTA AAT TAA TGC GCG CCT TGG TGT TGG CTC CCG TAT |
| CYP-9aF | 19 | TAC GGG AGC CAA CAC CAC TTG TTT TGC CTT GAT ATT CTC CTA TAT TGC CCA AGA GAG CAG GTG TGA CGG AT |
| CYP-9aR | 20 | ATC CGT CAC ACC TGC TCT CTT GGG CAA TAT AGG AGA ATA TCA AGG CAA AAC AAG TGG TGT TGG CTC CCG TA |
| CYP-11F | 21 | ATA CGG GAG CCA ACA CCA CGC GGC TCC TTT ATT TGC CAG ATT TAC ATG AAA GGT AGA GCA GGT GTG ACG GAT |

-continued

| Clone Name | SEQ ID NO. | DNA Aptamer Sequence |
|---|---|---|
| CYP-11R | 22 | ATC CGT CAC ACC TGC TCT ACC TTT CAT GTA AAT CTG GCA AAT AAA GGA GCC GCG TGG TGT TGG CTC CCG TAT |
| CYP-12aF | 23 | ATA CGG GAG CCA ACA CCA TCA ATC TAT ACT CCC GGT TCA CTA ATG TAC TCA AGC AGA GCA GGT GTG ACG GAT |
| CYP-12aR | 24 | ATC CGT CAC ACC TGC TCT GCT TGA GTA CAT TAG TGA ACC GGG AGT ATA GAT TGA TGG TGT TGG CTC CCG TAT |
| CYP-12bF | 25 | ATA CGG GAG CCA ACA CCA CTC GGA TAT CCC CTT TAT CTT TCC GAT TCG TGT CGA GAG CAG GTG TGA CGG AT |
| CYP-12bR | 26 | ATC CGT CAC ACC TGC TCT CGA CAC GAA TCG AAA GA TAA AGG GGA TAT CCG AGT GGT GTT GGC TCC CGT AT |
| CYP-13aF | 27 | ATA CGG GAG CCA ACA CCA TGG GGG GTA CTA AAT TGG T AGG GGG TTG TTC TTG AGA GCA GGT GTG ACG GAT |
| CYP-13aR | 28 | ATC CGT CAC ACC TGC TCT CAA GAA CAA CCC CCT ACC AAT TTA AGT ACC CCC CA TGG TGT TGG CTC CCG TAT |
| CYP-13bF | 29 | ATC CGT CAC ACC TGC TCT CAC ATC CAC CTA GTG GTC TTG AGG CCT CGT TCT GAG TGG TGT TGG CTC CCG TAT |
| CYP-13bR | 30 | ATA CGG GAG CCA ACA CCA CTC AGA ACG AGG CCT CAA GAC CAC TAG GTG GAT GTG AGA GCA GGT GTG ACG GAT |
| CYP-14F | 31 | ATA CGG GAG CCA ACA CCA GTG AGG ACT AAC GGG TTA AAT AAC ATG CTG AGC TGT AGA GCA GGT GTG ACG GAT |
| CYP-14R | 32 | ATC CGT CAC ACC TGC TCT ACA GCT CAG CAT GTT ATT TAA CCC GTT AGT CCT CAC TGG TGT TGG CTC CCG TAT |
| CYP-15F | 33 | ATA CGG GAG CCA ACA CCA TGC CAT TCA GGT TGT CAC CAA TCC GCA TTC GCG AAC AGA GCA GGT GTG ACG GAT |
| CYP-15R | 34 | ATC CGT CAC ACC TGC TCT GTT CGC GAA TGC GGA TTG GTG ACA ACC TGA ATG GCA TGG TGT TGG CTC CCG TAT |
| CYP-16F | 35 | ATA CGG GAG CCA ACA CCA TGA GCT CAC TTC TGC ACC CTC TAC TTC CGC CCC TCC AGA GCA GGT GTG ACG GAT |
| CYP-16R | 36 | ATC CGT CAC ACC TGC TCT GGA GGG GCG AAA GTA GAG GT GCA GAA GTG AGC TCA TGG TGT TGG CTC CCG TAT |
| CYP-17aF | 37 | ATA CGG GAG CCA ACA CCA GGG GGA GTA AGA GAG ACA GAC GCA GGA TAT TCG GGC AGA GCA GGT GTG ACG GAT |
| CYP-17aR | 38 | ATC CGT CAC ACC TGC TCT GCC CGA ATA TCC TGC GTC TGT CTC TCT TAC TCC CCC TGG TGT TGG CTC CCG TAT |
| CYP-17bF | 39 | ATA CGG GAG CCA ACA CCA CGC CGC TGT AGA TCC AGA CTG TAA TGT TCC ATC GGT AGA GCA GGT GTG ACG GAT |
| CYP-17bR | 40 | ATC CGT CAC ACC TGC TCT ACC GAT GGA ACA TTA CAG TCT GGA TCT ACA GCG GCG TGG TGT TGG CTC CCG TAT |
| CYP-18F | 41 | ATA CGG GAG CCA ACA CCA CTA TTT GCG TTG CAC ATT ACC TGA CAA CTT AAC TGG AGA GCA GGT GTG ACG GAT |
| CYP-18R | 42 | ATC CGT CAC ACC TGC TCT CCA GTT AAG TTG TCA GGT AAT GTG CAA CGC AAA TAG TGG TGT TGG CTC CCG TAT |
| CYP-19F | 43 | ATA CGG GAG CCA ACA CCA ACA AAC GAT TCA ATC AAC GTC CCA GAC CAT GGG TTC AGA GCA GGT GTG ACG GAT |
| CYP-19R | 44 | ATC CGT CAC ACC TGC TCT GAA CCC ATG GTC TGG GAC GTT GAT TGA ATC GTT TGT TGG TGT TGG CTC CCG TAT |
| CYP-21F | 45 | ATA CGG GAG CCA ACA CCA GAA CGG ATG GGG CTT ATG ATA TAG GTG AGA ACG GGT AGA GCA GGT GTG ACG GAT |
| CYP-21R | 46 | ATC CGT CAC ACC TGC TCT ACC CGT TCT CAC CTA TAT CAT AAG CCC CAT CCG TTC TGG TGT TGG CTC CCG TAT |
| CYP-22aF | 47 | ATA CGG GAG CCA ACA CCA GTG TCA ACA AGA TCC AAT TTT AGA CAA CAG AGC ACC AGA GCA GGT GTG ACG GAT |

| Clone Name | SEQ ID NO. | DNA Aptamer Sequence |
|---|---|---|
| CYP-22aR | 48 | ATC CGT CAC ACC TGC TCT GGT GCT CTG TTG TCT AAA ATT GGA TCT TGT TGA CAC TGG TGT TGG CTC CCG TAT |
| CYP-22bF | 49 | ATA CGG GAG CCA ACA CCA CGT TAA GAC CGC GAA ATG GTG CCA CAA CGA GTT TGG AGA GCA GGT GTG ACG GAT |
| CYP-22bR | 50 | ATC CGT CAC ACC TGC TCT CCA AAC TCG TTG TGG CAC CAT TTC GCG GTC TTA ACG TGG TGT TGG CTC CCG TAT |
| CYP-22cF | 51 | ATA CGG GAG CCA ACA CCA TGC CTG TAT GAC GTG TTT CCT AAC TTG TTG ATC CCT AGA GCA GGT GTG ACG GAT |
| CYP-22cR | 52 | ATC CGT CAC ACC TGC TCT AGG GAT CAA CAA GTT AGG AAA CAC GTC ATA CAG GCA TGG TGT TGG CTC CCG TAT |
| CYP-23F | 53 | ATA CGG GAG CCA ACA CCA CAA CAA CAT TAA CTC TAT TCC CAT AAA TCA TTA TAC AGA GCA GGT GTG ACG GAT |
| CYP-23R | 54 | ATC CGT CAC ACC TGC TCT GTA TAA TGA TTT ATG GGA ATA GAG TTA ATG TTG TTG TGG TGT TGG CTC CCG TAT |
| CYP-24aF | 55 | ATA CGG GAG CCA ACA CCA CAG ATG CGT ACC TCC CCA AAG TCC CGA TCA GTT GCC AGA GCA GGT GTG ACG GAT |
| CYP-24aR | 109 | ATC CGT CAC ACC TGC TCT GGC AAC TGA TCG GGA CTT TGG GGA GGT ACG CAT CTG TGG TGT TGG CTC CCG TAT |
| B13-1a/4/6/15/17/19/20F | 56 | ATA CGG GAG CCA ACA CCA CAA AGT TTA GCG TTA TGC AAC TCC CCC TTA TAC TCG AGA GCA GGT GTG ACG GAT |
| B13-1a/4/6/15/17/19/20R | 57 | ATC CGT CAC ACC TGC TCT CGA GTA TAA GGG GGA GTT GCA TAA CGC TAA ACT TTG TGG TGT TGG CTC CCG TAT |
| B13-1bF | 58 | ATA CGG GAG CCA ACA CCA CCA CCG ACT ACC CAG AAC CCG TTC TTC CCA CCA TGC AGA GCA GGT GTG ACG GAT |
| B13-1bR | 59 | ATC CGT CAC ACC TGC TCT GCA TGG TGG GAA GAA CGG GTT CTG GGT AGT CGG TGG TGT TGG CTC CCG TAT |
| B13-2F | 60 | ATA CGG GAG CCA ACA CCA AAA TTA ACA ACG CTG AAT TTA GAT TTG TAC TGC CGT AGA GCA GGT GTG ACG GAT |
| B13-2R | 61 | ATC CGT CAC ACC TGC TCT ACG GCA GTA CAA ATC TAA ATT CAG CGT TGT TAA TTT TGG TGT TGG CTC CCG TAT |
| B13-5F | 62 | ATA CGG GAG CCA ACA CCA CAG CAT GGC CGG TTA AGT TGA GAC GAT TGT ACT TTA AGA GCA GGT GTG ACG GAT |
| B13-5R | 63 | ATC CGT CAC ACC TGC TCT TAA AGT ACA ATC GTC TCA ACT TAA CCG GCC ATG CTG TGG TGT TGG CTC CCG TAT |
| B13-8F | 64 | ATA CGG GAG CCA ACA CCA GCG AAG CCA AAA CTG GTC GGG CCG ACG GGA TTC GTT AGA GCA GGT GTG ACG GAT |
| B13-8R | 65 | ATC CGT CAC ACC TGC TCT AAC GAA TCC CGT CGG CCC GAC CAG TTT GGC TTC GCG TGG TGT TGG CTC CCG TAT |
| B13-9F | 66 | ATA CGG GAG CCA ACA CCA CCT CAA CGC CCC TTA TAC CAC GAG CTT CCC CCC CCA GAG CAG GTG TGA CGG AT |
| B13-9R | 67 | ATC CGT CAC ACC TGC TCT GGG GGG GGA AGC TCG TGG TAT AAG GGG CGT TGA GGT GGT GTT GGC TCC CGT AT |
| B13-10aF | 68 | ATA CGG GAG CCA ACA CCA CAT CCT TAT CAG CCA AGA ACT TAT ACT GTC AGC CTA GA GCA GGT GTG ACG GAT |
| B13-10aR | 69 | ATC CGT CAC ACC TGC TCT AGG CTG GAC AGT ATA AGT TCT TGG CTG ATA AGG ATG TGG TGT TGG CTC CCG TAT |
| B13-10bF | 70 | ATA CGG GAG CCA ACA CCA GCC CAC TGC CAC GAT ATA TGC GCA ACC GCT GTC CGC AGA GCA GGT GTG ACG GAT |
| B13-10bR | 71 | ATC CGT CAC ACC TGC TCT GCG GAC AGC GGT TGC GCA TAT ATC GTG CAG TGG GCT TGG TGT TGG CTC CCG TAT |
| B13-11F | 72 | ATA CGG GAG CCA ACA CCA TTG CGA TTC GGC AGG GCA GGG TCG TAA ATC CTA CAT AGA GCA GGT GTG ACG GAT |

-continued

| Clone Name | SEQ ID NO. | DNA Aptamer Sequence |
|---|---|---|
| B13-11R | 73 | ATC CGT CAC ACC TGC TCT ATG TAG GAT TTA CGA CCC TGC CCT GCC GAA TCG CAA TGG TGT TGG CTC CCG TAT |
| B13-12F | 74 | ATA CGG GAG CCA ACA CCA CAC CAG CTA CTC GAG CAC CAT ATG AGA TTC AAT GGC AGA GCA GGT GTG ACG GAT |
| B13-12R | 75 | ATC CGT CAC ACC TGC TCT GCC ATT GAA TCT CAT ATG GTG CTC GAG TAG CTG GTG TGG TGT TGG CTC CCG TAT |
| B13-13F | 76 | ATA CGG GAG CCA ACA CCA CTT GTC CCC CAT CAG CAC CAT CTC CAT GCT CCT GGC AGA GCA GGT GTG ACG GAT |
| B13-13R | 77 | ATC CGT CAC ACC TGC TCT GCC AGG AGC ATG GAG ATG GTG CTG ATG GGG GAC AAG TGG TGT TGG CTC CCG TAT |
| B13-16F | 78 | ATA CGG GAG CCA ACA CCA CTC TCC CCG CGA GTT TAC CTG TAA ACA CAA CGC ATC AGA GCA GGT GTG ACG GAT |
| B13-16R | 79 | ATC CGT CAC ACC TGC TCT GAT GCG TTG TGT TTA CAG GTA AAC TCG CGG GGA GAG TGG TGT TGG CTC CCG TAT |
| H9-1/7/8b/9a/13/1518aF | 80 | ATA CGG GAG CCA ACA CCA TCC AAT GAG GCC ATG GAC CGG TAA ACT CGG ACG CGC AGA GCA GGT GTG ACG GAT |
| H9-1/7/8b/9a/13/1518aR | 81 | ATC CGT CAC ACC TGC TCT GCG CGT CCG AGT TTA CCG TCC CAT GGC CTC ATT GGA TGG TGT TGG CTC CCG TAT |
| H9-2/4-6/8a/9b/14/20F | 82 | ATA CGG GAG CCA ACA CCA CAA AGT TTA GCG TTA TGC AAC TCC CCC TTA TAC TCG AGA GCA GGT GTG ACG GAT |
| H9-2/4-6/8a/9b/14/20R | 83 | ATC CGT CAC ACC TGC TCT CGA GTA TAA GGG GGA GTT GCA TAA CGC TAA ACT TTG TGG TGT TGG CTC CCG TAT |
| H9-3/19F | 84 | ATA CGG GAG CCA ACA CCA CCG AAT GTG CTG CAG GAC TAA TCT GGA TGG CCA TGC AGA GCA GGT GTG ACG GAT |
| H9-3/19R | 85 | ATC CGT CAC ACC TGC TCT GCA TGG CCA TCC AGA TTA GTC CTG CAG CAC ATT CGG TGG TGT TGG CTC CCG TAT |
| H9-10aF | 86 | ATA CGG GAG CCA ACA CCA CCG AAT GTG CTG CAA GAC TAA TCT GGA TGG CCA TGC AGA GCA GGT GTG ACG GAT |
| H9-10aR | 87 | ATC CGT CAC ACC TGC TCT GCA TGG CCA TCC AGA TTA GTC TTG CAG CAC ATT CGG TGG TGT TGG CTC CCG TAT |
| H9-12F | 88 | ATA CGG GAG CCA ACA CCA CGT CAG GAC CTC CAT CGC CCG GGC CCG CCG CCG CTG AGA GCA GGT GTG ACG GAT |
| H9-12R | 89 | ATC CGT CAC ACC TGC TCT CAG CGG CGG CGG GCC GGG GCG ATG GAG GTC CTG ACG TGG TGT TGG CTC CCG TAT |
| H9-16F | 90 | ATA CGG GAG CCA ACA CCA TGA AGT GCG GTG TCG CTC TAA CTG ACG TAT GAA AGA GCA GGT GTG ACG GAT |
| H9-16R | 91 | ATC CGT CAC ACC TGC TCT TTC ATA CGT CAG TTA GAG CGA CAC CGC ACT TCA TGG TGT TGG CTC CCG TAT |
| H9-18bF | 92 | ATA CGG GAG CCA ACA CCA TGT CTT AGT CCG ATA CTA ACG TGC CCC TTG TCC CCA GAG CAG GTG TGA CGG AT |
| H9-18bR | 93 | ATC CGT CAC ACC TGC TCT GGG GAC AAG GGG CAC GTT AGT ATC GGA CTA AGA CAT GGT GTT GGC TCC CGT AT |
| H13-1/2-4/6-8/14-18/20F | 94 | ATA CGG GAG CCA ACA CCA CAA AGT TTA GCG TTA TGC AAC TCC CCC TTA TAC TCG AGA GCA GGT GTG ACG GAT |
| H13-1/2-4/6-8/14-18/20R | 95 | ATC CGT CAC ACC TGC TCT CGA GTA TAA GGG GGA GTT GCA TAA CGC TAA ACT TTG TGG TGT TGG CTC CCG TAT |
| H13-5F | 96 | ATA CGG GAG CCA ACA CCA CGT AAG TGA CCC CGC GGT CAG CAA TTA ACA CCA GGG AGA GCA GGT GTG ACG GAT |
| H13-5R | 97 | ATC CGT CAC ACC TGC TCT CCC TGG TGT TAA TTG CTG ACC GCG GGG TCA CTT ACG TGG TGT TGG CTC CCG TAT |
| H13-9/19F | 98 | ATA CGG GAG CCA ACA CCA CCG AAT GTG CTG CAA GAC TAA TCT GGA TGG CCA TGC AGA GCA GGT GTG ACG GAT |

-continued

| Clone Name | SEQ ID NO. | DNA Aptamer Sequence |
|---|---|---|
| H13-9/19R | 99 | ATC CGT CAC ACC TGC TCT GCA TGG CCA TCC AGA TTA GTC TTG CAG CAC ATT CGG TGG TGT TGG CTC CCG TAT |
| H13-11F | 100 | ATA CGG GAG CCA ACA CCA CTC ACA CGC CTA GCG TCA CGG TCC CTC CCC ACC CCC AGA GCA GGT GTG ACG GAT |
| H13-11R | 101 | ATC CGT CAC ACC TGC TCT GGG GGT GGG GAG GGA CCG TGA CGC TAG GCG TGT GAG TGG TGT TGG CTC CCG TAT |
| H13-12F | 102 | ATA CGG GAG CCA ACA CCA TGT TAC ATC AAC TGC ATG AAG ACG AGG AAT GTG ATG AGA GCA GGT GTG ACG GAT |
| H13-12R | 103 | ATC CGT CAC ACC TGC TCT CAT CAC ATT CCT CGT CTT CAT GCA GTT GAT GTA ACA TGG TGT TGG CTC CCG TAT |
| H13-13F | 104 | ATA CGG GAG CCA ACA CCA ATG TGA TCC GAC GTA CAC AGG CCG AGC GCT TCT AGT AGA GCA GGT GTG ACG GAT |
| H13-13R | 105 | ATC CGT CAC ACC TGC TCT ACT AGA AGC GCT CGG CCT GTG ACG TCG GAT CAC ATT GGT GTT GGC TCC CGT AT |

Clone names are derived as follows. B means a biotinylated-HODE used for immobilization on streptavidin. H-9 and B (biotinylated) 13 or H-13 mean 9 and 13 HODE isomers with or without biotin added. All HODEs were obtained from Cayman Chemical Co. Slashes with numbers and letters in between which indicate that the sequence emerged in more than clone (e.g., was fairly common in the final selected pool of aptamers). F=forward primed and R=reverse primed on the ds plasmid carrier. All sequences are written from 5' to 3' from left to right. Sequences (B13-9R and H9-3/19F) were shown to be of highest affinity in the ELASA (ELISA-like) plate screening assays (done in triplicate).

DNA ligand (aptamer) sequences are derived by iterative cycles of affinity-based selection, washing, heated elution, and polymerase chain reaction ("PCR") amplification of bound DNA ligands from a randomized library using immobilized target analytes for affinity selection and PCR amplification followed by cloning and Sanger dideoxynucleotide DNA sequencing. Sanger dideoxynucleotide sequencing refers to DNA chain termination due to a lack of a 3' hydroxyl (—OH) group to link incoming bases to during DNA synthesis followed by automated fluorescence reading of the DNA sequence from an electrophoresis gel containing all of the terminated DNA fragments. DNA sequencing may be accomplished by PCR doped with dideoxynucleotides lacking hydroxyl groups at the 2' and 3' sugar ring positions and thereby disallowing chain formation. PCR refers to the enzymatic amplification or copying of DNA molecules with a thermo-stable DNA polymerase such as *Thermus aquaticus* polymerase (Taq) with known "primer" regions or short oligonucleotides of known sequence that can hybridize to a longer target DNA sequence to enable priming of the chain reaction (exponential doubling of the DNA target copy number with each round of amplification). A randomized library can be chemically synthesized by linking together the four deoxynucleotide triphosphate bases (adenine; A, cytosine; C, guanine; G, and thymine; T) in equal amounts (25% each), so that a combinatorial oligonucleotide arises with sequence diversity equal to 4 raised to the nth power ($4^n$) where n is the desired length of the randomized region in bases. In other words, if position 1 in an oligonucleotide is allowed to consist of A, C, G, or T (diversity=4) by equal availability of all 4 bases and these 4 possibilities are multiplied by each base linking to 4 more possible bases at position 2, then this process yields 16 possible 2-base oligonucleotides (i.e., AA, AC, AG, AT, CA, CC, CG, CT, GA, GC, GG, GT, TA, TC, TG, TT) and so on for the entire chosen length (n) of the randomized region. This combinatorial progression displays immense diversity as a function of oligonucleotide chain length. For example, an oligonucleotide decamer of 10 base length could be expected to contain $4^n=4^{10}$ or 1,048,576 unique DNA sequences from which to chose or select one or more DNA sequences that bind a given immobilized target analyte with the strongest affinities. The randomized oligonucleotide or DNA is designed to be flanked on either side by short primer regions of known and fixed sequences to enable PCR amplification (exponential copying) of the rare sequences that are selected from the random library by binding to the target after the non-binding members of the random library are washed away (not selected).

HODE or Linoleic Acid Immobilization Techniques

General methods for developing DNA ligands or aptamers against immobilized small molecules such as linoleic acid and its oxidized metabolites (OLAMs or hydroxyoctadecadieneoic acids; HODES) are as follows. Racemic mixtures HODE isomers, in particular (±) 9-HODE and (±)13-HODE are obtained from Cayman Chemical Co. (Ann Arbor, Mich.) at 98% purity in ethanol at 1 µl. Linoleic acid and HODE isomers are individually immobilized on primary amine-coated Dynal M270 (2.7 micron diameter) magnetic microbeads (MBs; Invitrogen/Life Technologies, Inc.) by a carbodiimide linkage between the carboxyl group of the HODE and the amine group coating the MB. More specifically, EDC or EDAC (1-ethyl-3-(3-dimethylaminopropyl) carbodiimide) is dissolved in deionized water at 1 mg/ml and filter sterilized. Two hundred µl of stock EDC solution is added to a polyethylene microfuge tube along with 200 µl of amine-M270 MBs ($\sim 4 \times 10^8$ total MBs), in a final volume of 1 ml of 50 mM MES (2-(N-morpholino)ethanesulfonic acid, pH ~6.0) and 50 µl of either 9-HODE or 13-HODE (50 µg of HODE) which is mixed end over end gently at 37° C. overnight. The next day, the HODE-conjugated MBs are washed three times in 1 ml of sterile phosphate buffered saline (PBS, pH 7.2-7.4) at room temperature (RT; ~25° C.) for 2 minutes per wash and collected using a magnetic collection rack. Supernates are siphoned off of the magnetically collected MB pellet and HODE-MBs are resuspended in sterile PBS and stored at 4° C. until used for aptamer affinity selection.

Alternatively, 5 µg of a biotinylated version of 13-HODE (Cayman Chemical Co.) are immobilized onto 15 µl streptavidin-coated M270 (2.7 micron diameter) magnetic microbeads (~1.33×10$^5$ SAv-MBs) for 20 minutes at RT with gentle mixing followed by three 1 ml washes in sterile PBS using a magnetic collection rack. Alternative methods include, but are not limited to, the use of the Mannich formaldehyde condensation reaction using DADPA-activated MBs (Bioclone, Inc., San Diego, Calif.) or PharmaLink™ columns from Pierce Chemical Co. (Thermo Scientific, Inc.) or other immobilization techniques involving chemically or ultraviolet-activated columns, filter membranes or microbeads.

DNA Ligand (Aptamer) Selection and Generation

Target molecule (HODE)-conjugated MBs (or target-MBs) are collected for 2 minutes in a magnetic collection device using an external magnet and the supernate is carefully withdrawn with a pipette tip. Target-MBs are then resuspended by vortexing briefly in 1× Binding Buffer (1×BB; 0.5M NaCl, 10 mM Tris-HCl, and 1 mM MgCl$_2$, pH 7.5-7.6,) and washed by agitation for 5 minutes. MBs are collected and washed three times in this manner and then resuspended in 1 ml of 1×BB.

MB-based DNA ligand or aptamer development is then performed using a template library sequence such as: 5'-ATC-CGTCACACCTGCTCT-N$_{36}$-TGGTGTTGGCTCCCG-TAT-3', (SEQ ID NO. 106) where N$_{36}$ represents the randomized 36-base region of the DNA library (maximal theoretical sequence diversity=4$^{36}$ with a more practical diversity limit of ~10$^{15}$ sequences). Primer sequences are: 5'-ATACGG-GAGCCAACACCA-3' (SEQ ID NO. 107, designated forward) and 5'-ATCCGTCACACCTGCTCT-3' (SEQ ID NO. 108, designated reverse) to prime the template and nascent strands for PCR, respectively. The random library is reconstituted in 500 µl of sterile nuclease-free water and heated to 95° C. for 5 minutes to ensure that the DNA library is completely single-stranded and linear. The hot DNA library solution is added to 100 µl of target-MBs (2×10$^8$ beads) with 600 µl of sterile 2× Binding Buffer (2×BB). The DNA library and target-MB suspension (1.2 ml) is mixed at room temperature (RT, approximately 25° C.) for 1 hour. Target-MBs with any bound DNA (round 1 aptamers) are magnetically collected. The DNA-target-MB complexes are washed three times in 400 µl of sterile 1×BB. Following the third wash, the DNA-target-MB pellet (about 75 µl) is used in a PCR reaction to amplify the bound DNA as follows. The MB pellet is split into 15 µl aliquots and added to five pre-made PCR tubes which contain most of the nonperishable ingredients of a PCR reaction beneath a wax seal. A total of 3 µl of 1:10 primer mix (10% forward primer plus 10% reverse primer) in nuclease-free deionized water or ~20 nanomoles of each primer per ml plus 1 µl (5 U) of Taq DNA polymerase and 5 µl of 2 mM MgCl$_2$ are added to each of the five tubes. PCR reactions are supplemented with 0.5 µl of *E. coli* single-strand binding protein (SSBP, Stratagene Inc., La Jolla, Calif.) to inhibit high molecular weight concatamer (end to end aggregates of the DNA ligands) formation. PCR is carried out as follows: an initial 95° C. phase for 5 minutes, followed by 20 cycles of 1 minute at 95° C., 1 minute at 53° C., and 1 minute at 72° C. followed by a 72° C. completion stage for 7 minute, and refrigeration at 4° C. This constitutes the first of multiple rounds of MB-aptamer development. Iterations of the MB-aptamer development process are repeated until the desired affinity or assay sensitivity and specificity are achieved. Typically, 5-10 rounds of the MB-aptamer development process are required to achieve low ng/ml detection of target analytes. To begin the second round and all subsequent rounds, 4 complete tubes of the 5 original PCR tubes are heated to 95° C. for 5 minutes to release bound DNA from the target-MBs. The fifth tube is always retained and refrigerated as a back-up for that round of the aptamer generation process. All available DNA (25 µl per tube) is siphoned out of the hot tubes without removing the target-MBs before the tubes cool significantly and the DNA is pooled. The 100 µl of hot DNA is added to 100 µl of fresh target-MBs in 200 µl of 2×BB and allowed to mix for 1 hr at RT. Thereafter, the selection and amplification process are repeated for nine more rounds (10 total rounds of selection) with checking for 72 by aptamer PCR products by ethidium bromide-stained 2% agarose electrophoresis after each round. Following the last round of aptamer development, aptamers are cloned into chemically competent *E. coli* using a cloning kit from Lucigen Corp. (Middleton, Wis.) and clones are sent to Sequetech, Inc. (Mountain View, Calif.) for DNA sequencing using rolling circle amplification and a high heat-sequencing protocol for sequences containing a high GC content.

Screening of Aptamers for Highest Affinity in ELISA-Like Plate Assay ("ELASA")

To evaluate, screen, and rank aptamers based on affinity against their cognate HODE isomers, two different approaches are used. The first involved the use of Corning Costar Universal Bind™ microplates (No. 2503) for ultraviolet (UV) immobilization of 200 ng/well of unlabeled HODES to the plate's surface (Bruno et al., 2008 and 2009) using 0.2 Joules/cm$^2$ in a UV crosslinker oven for 15 minutes. The second involved streptavidin (SAv)-coated microwell strips (Nunc, Inc. Catalogue #436020) in which 400 ng of the biotinylated-13-HODE are immobilized for 30 minutes at RT with gentle mixing in 200 µl of PBS per well.

Plates or wells are decanted and washed three times in 250 µl of 1×BB. Each of the different 5'-biotinylated aptamers raised against the target is dissolved in 1×BB at 1.00 nmole per 100 microliters and applied to their corresponding plate wells for 1 hour at RT with gentle mixing on an orbital shaker. The plate is decanted and washed three times in 250 µA of 1×BB for at least 5 minutes per wash with gentle mixing. One hundred µl of a 1:2,000 dilution of SAv-peroxidase from a 5 mg/ml stock solution in 1×BB is added per well for 30 minutes at RT with gentle mixing. The plate is decanted and washed three times with 250 µl of 1×BB per well as before.

One hundred µl of ABTS (2,2'-azino-bis(3-ethylbenzthiazoline-6-sulphonic acid) substrate with stabilized hydrogen peroxide (Kirkegaard Perry Laboratories, Inc., Gaithersburg, Md.) is added per well for 10 minute at RT. Various deletion control wells without biotinylated aptamers or SAv-peroxidase are set up and evaluated to establish background levels as well. Finally absorbance is quantified using a microplate reader with 405 nm optical filter.

Example 1

Results of ELASA Screening Trials

Table 1 demonstrates that after three separate ELASA trials having low background controls (Absorbance at 405 nm<<1.0) using either the UV or streptavidin plate immobilization method, two anti-HODE aptamer sequences consistently emerged with the top two to three strongest absorbance signals. These aptamers were: H9-3/19F and B13-9R for the 9-HODE and biotinylated 13-HODE targets respectively and they proceeded into animal testing.

TABLE 1

Results of 3 ELASA Ranking Trials for 9-HODE and 13-HODE Aptamers

| Rank | Trial 1 Aptamer | Trial 1 Abs 405 nm | Trial 2 Aptamer | Trial 2 Abs 405 nm | Trial 3 Aptamer | Trial 3 Abs 405 nm |
|---|---|---|---|---|---|---|
| 1 | H9-3/19F | 2.081 | B13-9R | 1.885 | B13-9R | 1.964 |
| 2 | H9-3/19R | 1.571 | H9-3/19F | 1.648 | H9-3/19F | 1.640 |
| 3 | B13-9R | 1.549 | B13-1a/4/6/15/17/19/20R | 1.595 | B13-1/2-4/6-8/14-18/20F | 1.387 |
| 4 | B13-8F | 1.490 | B13-10b R | 1.214 | B13-12R | 1.310 |
| 5 | H13-12F | 1.442 | H13-1/2-4/6-8/14-18/20F | 1.199 | H9-2/4-6/8a/9b/14/20F | 1.249 |

Notes:
All values represent Absorbance (Abs) at 405 nm 10-15 minutes after final addition of ABTS substrate.
Abbreviations:
H; HODE,
B; biotinylated aptamer,
F; forward primed,
R; reverse primed, and numbers indicate the type of HODE (9 or 13) or the aptamer clone number.
Slashes indicate more than one clone contained that particular aptamer sequence.

Top 2 Aptamer Sequences:

<SEQ ID NO. 84>
H9-3/19F:
5'-ATA CGG GAG CCA ACA CCA CCG AAT GTG CTG CAG GACTAA TCT GGA TGG CCA TGC AGA GCA GGT GTG ACG GAT

<SEQ ID NO. 67>
B13-9R:
5'-ATC CGT CAC ACC TGC TCT GGG GGG GGA AGC TCG TGG TAT AAG GGG CGT TGA GGT GGT GTT GGC TCC CGT AT-3'

SPR Analysis of H9-3/19F Aptamer and B13-9R Aptamer with 13(S)-HODE-Biotin

13(S)-HODE-Biotin was immobilized on a CM5 sensor chip utilizing biotin-streptavidin chemistry. Various concentrations of H9-3/19F aptamer (SEQ ID. NO. 84) were flowed through the Biacore X100 with 1×HBS-EP+ running buffer at a flow rate of 30 µl/min and allowed a contact time with the surface-bound ligand of 90 seconds, followed by a dissociation time set at 600 seconds. The following concentrations of aptamer were used: 20 µM, 40 µM, 60 µM and 80 µM. SPR analysis determined that the dissociation constant, $K_D$ for H9-3/19F aptamer (SEQ ID. NO. 84) was $1.29 \times 10^{-10}$ M.

13(S)-HODE-Biotin was immobilized on a CM5 sensor chip utilizing biotin-streptavidin chemistry. Various concentrations of B13-9R aptamer (SEQ ID. NO. 67) were flowed through the Biacore X100 with 1×HBS-EP+ running buffer at a flow rate of 30 µl/min and allowed a contact time with the surface-bound ligand of 90 seconds, followed by a dissociation time set at 600 seconds. The following concentrations of aptamer were used: 20 µM, 40 µM, 60 µM and 80 µM. SPR analysis determined that the dissociation constant, $K_D$ for B13-9R aptamer (SEQ ID. NO. 67) was $2.56 \times 10^{-9}$ M.

DNA or RNA aptamers that show high affinity for OLAMs may be bound to a compound that improves binding to plasma proteins, delivery to inflamed tissue and/or exerts intrinsic pharmacodynamic properties. In a further embodiment, aptamers that show high affinity for two or more different OLAMs may be linked together and may be further linked to a compound that improves binding to plasma proteins, delivery to inflamed tissue and/or exerts intrinsic pharmacodynamic properties.

With respect to pain and inflammation management, additional benefits may be gained if the plasma protein binding compound is also an anti-inflammatory compound, or has pain reducing properties. Examples of compounds that are plasma protein binding compounds and are pharmacologically active in inflamed/injured tissue include non-steroidal anti-inflammatory drugs ("NSAIDS"), antibiotics, local anesthetics, opiates, antihistamines, or steroids. Specific examples of NSAIDS that are plasma binding compounds include, but are not limited to: salicylates (e.g., aspirin (acetylsalicylic acid), diflunisal, and salsalate); propionic acid derivatives (e.g., ibuprofen, dexibuprofen, naproxen, fenoprofen, ketoprofen, dexketoprofen, flurbiprofen, oxaprozin, and loxoprofen); acetic acid derivatives (e.g., indomethacin, tolmetin, sulindac, etodolac, ketorolac, diclofenac, and nabumetone); enolic acid (oxicam) derivatives (e.g., piroxicam, meloxicam, tenoxicam, droxicam, lornoxicam, and isoxicam); and fenamic acid derivatives (fenamates) (e.g., mefenamic acid; meclofenamic acid; flufenamic acid; and tolfenamic acid. Other exemplary plasma protein binding compounds that also exhibit pain reducing properties or anti-inflammatory properties are antibiotics (e.g., clindamycin, erythromycin, or the sulphonamides), local anesthetics (e.g., bupivacaine), opiates (e.g., methadone), or steroids (e.g., prednisolone).

In an embodiment, the plasma protein binding compound, will bind to the plasma proteins in a pH-dependent fashion, such that binding would be reduced at lower pH values seen in tissue inflammation or injury. This would lead to increased free drug concentrations in the inflamed tissue and therefore improved pharmacodynamics. Examples of drugs that bind to plasma proteins in a pH-dependent fashion are biperiden, clindamycin, dexamethasone, fluoxetine, and nelfinavir.

In some embodiments, the plasma protein binding compound is covalently linked to a DNA or RNA aptamer that shows high affinity for OLAMs. The plasma protein binding compound may be covalently coupled to the 5' end, 3' end or an internal base. In one embodiment, one or more bases of the DNA or RNA aptamer that shows high affinity for OLAMs may be modified such that a linker molecule is covalently coupled to a portion of the base (e.g., the nucleobase). In one embodiment, one or more nucleobases may be modified by covalenelty attaching an amine linker to the nucleobase. An example of a thymine modified nucleotide is shown below:

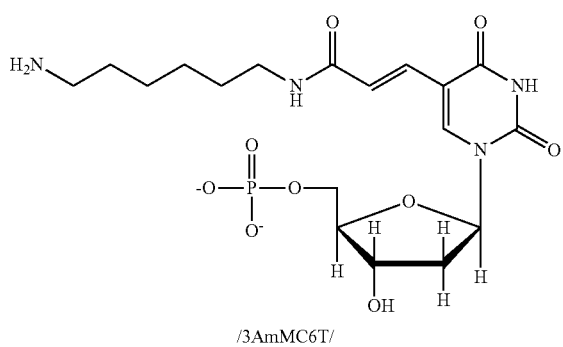

/3AmMC6T/

Other nucleotides may be modified in a similar manner. Modified nucleotides may be substituted with the unmodified nucleotide to be incorporated into the DNA or RNA aptamer that shows high affinity for OLAMs. The pendant amine group of the modified nucleotide may be used to covalently link a plasma protein binding compound to the aptamer.

In some embodiments, it may be desired to use a linker molecule to couple the pharmacologically active agent used to treat the inflammatory condition to a plasma protein binding compound. A linker molecule is generally any molecule that is used to covalently couple the drug to the plasma protein binding compound. In some embodiments, a linker may be a homobifunctional linker. Such compounds may have the general formula R—$(CH_2)_n$—R, where R is $CO_2H$, $NH_2$, OH, SH, CH=O, $CR^1$=O, CH=NH, or halogen; n is 1-20, and $R^1$ is $C_1$-$C_6$ alkyl). Alternatively, the linker may be a heterobifunctional linker. Such compounds may have the general formula $R^2$—$(CH_2)_n$—$R^3$, where $R^2$ and $R^3$ are different, and where each $R^2$ and $R^3$ is $CO_2H$, $NH_2$, OH, SH, CH=O, $CR^1$=O, CH=NH, or halogen; n is 1-20; and $R^1$ is $C_1$-$C_6$ alkyl. A linker molecule may covalently bond with at least one reactive functional group of the aptamer and at least one reactive functional group of the plasma protein binding compound. Specific linkers may be chosen for use such that plasma protein binding compound may be released under certain physiological conditions.

One example of a linkage that may be used to covalently link a plasma protein binding compound to a DNA or RNA aptamer that shows high affinity for OLAMs is shown in Scheme 1.

Scheme 1

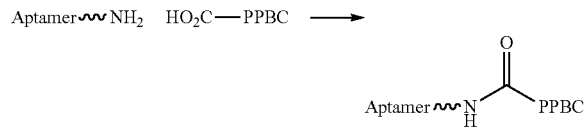

An aptamer may be modified, as discussed above, to have a pendant amino group linked to a nucleotide which is incorporated in the aptamer (e.g., at the 3' end). The amine functional group of the modified nucleotide may be reacted with a carboxylic acid functional group of a plasma protein binding compound to create a covalent amide bond coupling the aptamer to the plasma protein binding compound as shown in Scheme 1. Examples of plasma protein binding compounds that may be coupled to aptamers in this manner include NSAIDS, antihistamines, and steroids that have carboxylic acid functional groups. Examples of NSAIDS that have carboxylic acid functional groups that can be used to couple the NSAID to an aptamer include, but are not limited to: NSAID Salicylates (e.g., aspirin, diflunisal, and salsalate); NSAID Propionic Acid Derivatives (e.g., ibuprofen, dexibuprofen, naproxen, fenoprofen, ketoprofen, dexketoprofen, flurbiprofen, oxaprozin, andioxoprofen; NSAID Acetic Acid Derivatives (e.g., indomethacin, tolmetin, sulindac, etodolac, ketorolac, diclofenac, 6-methoxy-2-naphthyl acetic acid (an active metabolite of nabumetone), and licofelone); NSAID Fenamic Acid Derivatives (e.g., mefenamic acid, meclofenamic acid, flufenamic acid, and tolfenamic acid) and NSAID Coxibs (e.g., lumiracoxib). Examples of antihistamines that have carboxylic acid functional groups that can be used to couple the antihistamine to an aptamer include, but are not limited to: acrivastine; bilastine; cetirizine; fexofenadine; levocetirizine; and olopatadine.

In an exemplary procedure, Aptamer SEQ ID NO. 67 was modified by adding the nucleotide/3AmMC6T/to the 3' end of the aptamer to provide a $NH_2$ functional group for attachment of ibuprofen to the aptamer. Ibuprofen was modified by converting the carboxylic acid to the N-Hydroxysuccinimide ester. The NHS-ibuprofen was reacted with the modified aptamer in a DMSO/Water solution having a pH of about 8.2. After reaction was complete the samples were purified in nuclease-free deionized water through a Sephadex G25 column to yield the ibuprofen linked aptamer. Using the same procedure, Aptamer SEQ ID NO. 84 was also linked to ibuprofen.

Another example of a linkage that may be used to covalently link a plasma protein binding compound to a DNA or RNA aptamer that shows high affinity for OLAMs is shown in Scheme 2.

Scheme 2

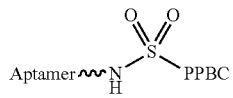

An aptamer may be modified, as discussed above, to have a pendant amino group linked to a nucleotide which is incorporated in the aptamer (e.g., at the 3' end). The amine functional group of the modified nucleotide may be reacted with a sulfonic acid functional group of a plasma protein binding compound to create a covalent sulfonamide bond coupling the aptamer to the plasma protein binding compound as shown in Scheme 2. Examples of plasma protein binding compounds that may be coupled to aptamers in this manner include NSAIDS, antihistamines, and steroids that have carboxylic acid functional groups. Examples of NSAIDS that have carboxylic acid functional groups that can be used to couple the NSAID to an aptamer include, but are not limited to: NSAID Coxibs (e.g., celecoxib; rofecoxib; valdecoxib; parecoxib; etoricoxib; firocoxib).

Another example of a linkage that may be used to covalently link a plasma protein binding compound to a DNA or RNA aptamer that shows high affinity for OLAMs is shown in Scheme 3 (R is typically an alkyl group or hydrogen).

Scheme 3

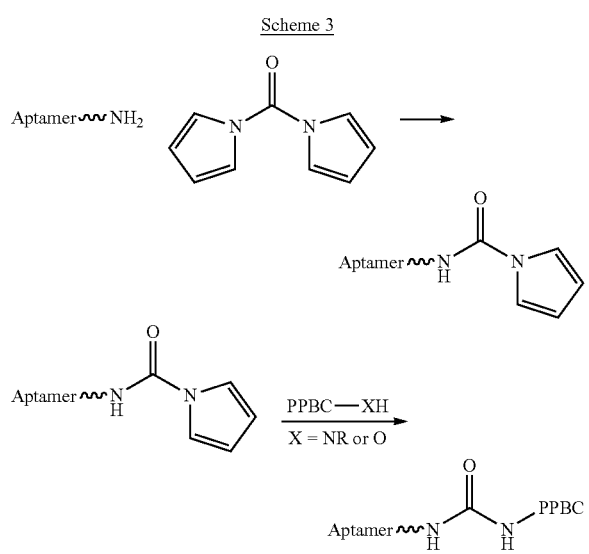

An aptamer may be modified, as discussed above, to have a pendant amino group linked to a nucleotide which is incorporated in the aptamer (e.g., at the 3' end). The amine functional group of the modified nucleotide may be reacted with carbonylimidazolide (or other suitable phosgene substitutes to create an intermediate imidazole urea. The intermediate imidazole urea may be reacted with a nucleophilic group of a plasma protein binding compound (e.g., —OH or —NH$_2$) to create a covalent urea bond coupling the aptamer to the plasma protein binding compound as shown in Scheme 3. Examples of plasma protein binding compounds that may be coupled to aptamers in this manner include NSAIDS, antihistamines, and steroids that have an amine or hydroxyl functional groups.

Examples of NSAIDS that have hydroxyl functional groups that can be used to couple the NSAID to an aptamer via a urea bond include, but are not limited to: NSAID Enolic Acid (Oxicam) Derivatives (e.g., piroxicam, meloxicam, tenoxicam, lornoxicam, and isoxicam). Examples of steroids that have hydroxyl functional groups that can be used to couple the steroid to an aptamer via a urea bond include Corticosteroids (e.g., hydrocortisone, glucocorticoid, tixocortol pivalate, prednisolone, methylprednisolone, prednisone, triamcinolone acetonide, triamcinolone, amcinonide (deacylated), budesonide, desonide, fluocinonide (deacylated), fluocinolone acetonide, betamethasone, dexamethasone, fluocortolone, halometasone, fluprednidene, and flunisolide. Some Corticosteroids include a hydroxyl functional group that is "protected" as an acyl group. In some embodiments, deacylated steroids may be coupled to an aptamer via a urea bond after deacylation. Examples of deacylated steroids that may be coupled to an aptamer via a urea bond after deacylation include, but are not limited to, amcinonide and fluocinonide. Examples of antihistamines that may be coupled to an aptamer via a urea bond include, but are not limited to, hydroxyzine and quetiapine.

Examples of antihistamines that have amine functional groups that can be used to couple the antihistamine to an aptamer via a urea bond include, but are not limited to desloratadine. Most antihistamines include a tertiary amine functional group that has at least one methyl group attached to the nitrogen of the tertiary amine functional group. Removal of the methyl group, either by modification of the antihistamine or intentional synthesis of the demethylated antihistamine, will yield a secondary amine that can be reacted according to Scheme 3 to form a urea bond. In some embodiments, demethylated antihistamine amines may be coupled to an aptamer via a urea bond. Examples of antihistamines that may be coupled to an aptamer via a urea bond in this manner include, but are not limited to, brompheniramine, bromazine, carbinoxamine, chlorpromazine, chlorphenamine, clemastine, cyproheptadine, dexbrompheniramine, dexchlorpheniramine, dimetindene, diphenhydramine, doxylamine, embramine, orphenadrine, pheniramine, phenyltoloxamine, promethazine, mepyramine, tripelennamine, triprolidine, nizatidine, and andranitidine.

In another embodiment, a small linker molecule may be used to couple the plasma protein binding compound to a DNA or RNA aptamer that shows high affinity for OLAMs is shown. In this embodiment, the same aminated nucleotide may be used to introduce a free amine functional group onto the aptamer. The amine may be coupled to a linking molecule that alters the functional group used for coupling. For example a dicarboxylic acid linker (e.g., a compound having the structure R—(CH$_2$)$_n$—R, where R is CO$_2$H and n is an integer between 1 and 20) may be used to change the amine functional group into a carboxylic acid group. One of the carboxylic acid groups may be reacted with the amine functional group of the modified nucleotide to form an amide bound coupling the linker to the nucleotide. The other carboxylic acid group may be reacted with oxygen or amine groups of the plasma protein binding compound to covalently link the PPBC to the nucleotide tide. In this way the nitrogen functionality of the nucleotide may be altered to a carboxylic acid, thus increasing the number of compounds that may be bound to the amine modified nucleotide.

Other linker molecules may be used to modify the functionality (e.g., amine) of the DNA or RNA aptamer that shows high affinity for OLAMs. For example, linker molecules having the general structure R$^2$—(CH$_2$)$_n$—R$^3$, where R$^2$ is CO$_2$H and R$^3$ is CO$_2$H, OH, SH, CH=O, or CR$^1$=O, or halogen; n is 1-10, and R$^1$ is C$_1$-C$_6$ alkyl). A linker molecule may covalently bond with at least one reactive functional group of the aptamer and at least one reactive functional group of the plasma protein binding compound. R$^2$ may form an amide bound with the amine functional group of the nucleotide. When R$^3$ is OH or SH, the linker may bind to a plasma protein binding compound through ester, thioester, ether or thioether bounds. When R$^3$ is CH=O, or CR$^1$=O, the linker may bind to an amine group of a plasma protein binding compound by an imine bond.

In an embodiment, aptamers that show high affinity for OLAMs may be bound to polyethylene glycol. In a further embodiment, aptamers or DNA sequences that show high affinity for two or more different OLAMs may be linked together and may be further linked to polyethylene glycol. Methods for attaching polyethylene glycol to nucleic acids are taught in the paper to Jäschke et al. "Synthesis and properties of oligodeoxyribonucleotide-polyethylene glycol conjugates" *Nucleic Acids Research*, 22:22, pp. 4810-4817, 1994, which is incorporated herein by reference.

In some embodiments, aptamers or DNA sequences that show high affinity for two or more different OLAMs may be linked together via a linker molecule. In some embodiments, it may be desired to use a linker molecule to couple the pharmacologically active agent used to treat the inflammatory condition to a plasma protein binding compound. A linker molecule is generally any molecule that is used to covalently couple two nucleic acids together. In some embodiments, a linker may be a homobifunctional linker. Such compounds may have the general formula R—(CH$_2$)$_n$—R, where R is CO$_2$H, NH$_2$, OH, SH, CH=O, CR$^1$=O, CH=NH, or halogen; n is 1-20, and R$^1$ is C$_1$-C$_6$ alkyl). Alternatively, the linker may be a heterobifunctional linker. Such compounds may have the general formula R$^2$—(CH$_2$)$_n$—R$^3$, where R$^2$ and R$^3$ are different, and where each R$^2$ and R$^3$ is CO$_2$H, NH$_2$, OH, SH, CH=O, CR$^1$=O, CH=NH, or halogen; n is 1-20, and R$^1$ is C$_1$-C$_6$ alkyl. A linker molecule may covalently bond with at least one reactive functional group of a first aptamer and at least one reactive functional group of a second aptamer. The resulting compound has the general structure:

Aptamer 1—Linker—Aptamer 2

In another embodiment, aptamers or DNA sequences that show high affinity for two or more different OLAMs may be linked together via a linker molecule and further linked to a pharmacologically active agent used to treat the inflammatory condition. In other embodiments, the linked aptamers by be further coupled to a plasma protein binding compound. Methods of coupling linked aptamers to pharmacologically active agents are the same as discussed above.

Generally the pharmacokinetics of an aptamer may be improved by coupling to a compound that improves binding to plasma proteins, delivery to inflamed tissue and/or exerts intrinsic pharmacodynamic properties. Coupling to the 3' end of an aptamer especially reduces the activity of serum Exonuclease I and lengthens the lifetime of aptamers in circulation. Adding weight to aptamers by coupling to other macromolecules such as proteins also retards aptamer clearance by the kidneys, liver and other major organs.

Serum stabilization of OLAM-targeting aptamers may also be achieved by attaching a blocking group to the 3' end of the aptamers. It has been shown that if you block the 3' end of a nucleic acid with a small molecule (e.g., biotin), you can decrease serum exonuclease activity. When larger molecules are attached to the 3' end, clearance of the conjugates by the kidneys or other major organs is reduced. In some embodiments, attachment of proteins to the 3' end of aptamers may improve the bioavailability of the aptamers. Procedures for the attachment of small molecules and proteins to the 3' end of aptamers are taught in U.S. Pat. No. 6,780,850 to Dougan et al.; U.S. Pat. No. 7,910,297 to Bruno et al. and in the paper to Bruno et al. "Selective Glutaraldehyde-Mediated Coupling of Proteins to the 3' adenine Terminus of Polymerase Chain Reaction Products" *Journal of Biomolecular Techniques,* 19(3), pp. 177-183, 2008, all of which are incorporated herein by reference.

In another embodiment, thioate aptamers may be produced that have a phosphorodithioate group (2 sulfurs replace the oxygens in phosphates in the nucleic acid backbone instead of phosphates). Examples of procedures for the synthesis of thioate aptamers are taught in U.S. Pat. No. 6,867,289 to Gorenstein et al., which is incorporated herein by reference.

In another embodiment, the base at the 3' or 5' end of an aptamer may be "inverted" as described in U.S. Pat. No. 6,197,944 to Walder et al., which is incorporated herein by reference.

Other methods of stabilizing aptamers and other OLAMs are described in the following publications, all of which are incorporated herein by reference: Wlotzka et al. "In vivo properties of an anti-GnRH Spiegelmer: An example of an oligonucleotide-based therapeutic substance class" *PNAS,* 99(13), pp. 8898-8902, 2002; Harding et al. "The immunogenicity of humanized and fully human antibodies. Residual immunogenicity resides in the CDR regions" *mAbs,* 2:3, pp. 256-265, 2010.

In some embodiments, a method of treating a pain, shock and/or inflammatory conditions may include administering an aptamer that inhibits cytochrome P-450 (CYP) enzyme sufficient to substantially inhibit and/or reduce the catalytic effect of multiple P450 isozymes capable of synthesizing oxidized linoleic acid metabolites (OLAMs). In some embodiments, the CYP aptamer inhibitor may be administered intravenously, orally, by inhalation, intra-nasally, topically (for burns or wounds), directly into the central nervous system (e.g., epidural), or any other method described herein or that will be known to those skilled in the art. In some embodiments, a method of treating pain, shock and/or inflammatory conditions may include administering a cytochrome P-450 (CYP) isoenzyme aptamer inhibitor sufficient to substantially inhibit or reduce the catalytic effect of enzyme EC 1.14.14.1 (aka: CYP2C9 and CYP2C19), EC 1.14.13.32/1.14.13.67/1.14.13.97/1.14.14.1 (CYP 3A4), EC 1.14.14.1 (CYP2J2), CYP27B1, CYP27C1, CYP2C18, CYP2E1, CYP39A1, CYP3A5, CYP3A7, CYP4B1, CYP4F12, CYP4F22, and CYP4F3.

Recent research has indicated that activation of TRPV1 by 9-HODE may have other roles in the body depending upon the expression of TRPV 1. TRPV 1 in the spinal cord may play an important role in maintenance of thermal and mechanical allodynia in inflammatory or other pain conditions. Depolarization of the spinal cord may lead to the release of 9-HODE and activation of TRPV1. 9-HODE in the spinal cord may lead to development of mechanical allodynia. Similar to injured peripheral tissues, depolarized spinal cord (with high potassium) may release compound(s) that have TRPV 1 agonist activity. Depolarized spinal cord superfusate may contain significantly higher amounts of 9-HODE. Moreover, activation of TRPV1 in the spinal cord by capsaicin (positive control) or by 9-HODE results in tactile allodynia that is completely reversible by a TRPV 1 antagonist. Thus, in some embodiments, the role of 9-HODE and similar linoleic acid oxidation products extends beyond heat-nociception.

Other research has shown elevated levels of OLAMs in atherosclerotic plaques. Thus, in some embodiments, DNA aptamers that inhibit and/or minimize the production of oxidized linoleic acid metabolites may be used to treat atherosclerotic plaques.

In some embodiments, a method may include treating shock and/or inflammation. The therapy used to treat any one case of shock depends upon the cause of the patient's hypoperfusional disorder. However, a disruption in cellular membrane integrity, leading to the release and oxidation of linoleic acid metabolites from stressed cells, is a process common to many if not most, cases of shock. These oxidized linoleic acid metabolites have paracrine and/or endocrine effects that act to worsen the symptoms of shock. A method as described herein may effectively delay the multi-organ failure associated with Refractory (Irreversible) shock. This therapeutic method may be used in many, if not most, cases of shock and save many lives.

In some embodiments, given the role of these metabolites in various other diseases (e.g., arthritis, pulmonary edema and shock), similar methods and antibodies or nucleic acid aptamers may be used in treating these conditions.

Figure 3:
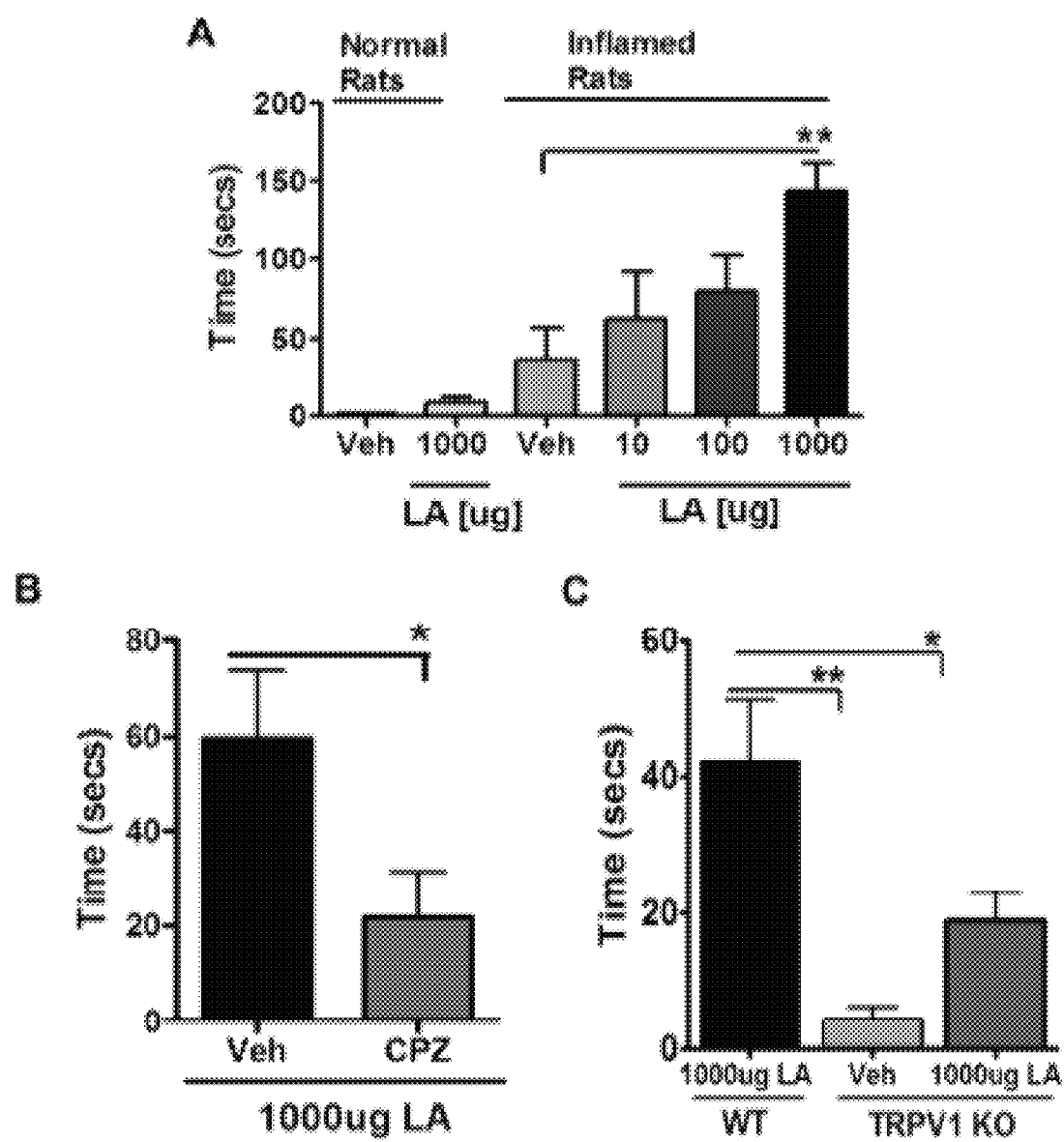
FIGS. 3A-C show that greater doses of OLAMs (in this case by giving linoleic acid) leads directly to increased pain.

The level of pain before and after treatment may therefore be assessed by measuring the level of one or more linoleic acid metabolites. In an embodiment, DNA or RNA aptamers or segments of aptamers (binding sites) that show high affinity for OLAMs may be used to diagnose the level of pain experienced by a subject. The DNA/RNA aptamers may be used in a variety of test methods including but not limited to, lateral flow or chromatographic test strips, ELISA-like enzymatic microplate assays, electrochemiluminescence (ECL), and fluorescence assays including standard intensity-based assays, lifetime or fluorescence decay assays, fluorescence resonance energy transfer (FRET) assays, fluorescence polarization and anisotropy assays. A variety of bodily fluids may be used for the test procedures including, but not limited to, blood serum, sputum or saliva, urine, cerebrospinal fluid, and interstitial fluid. Generally, the procedures will correlate the level of one or more linoleic acid metabolites to an arbitrary pain level scale. FIG. 3 shows that greater doses of OLAMs (in this case by giving linoleic acid) leads directly to increased pain.

Any suitable route of administration may be employed for providing a subject with an effective dosage of the compounds described herein. For example, oral, subcutaneous, rectal, intra-articular, topical, parenteral, ocular, pulmonary, nasal, and the like may be employed. Dosage forms include tablets, troches, dispersions, suspensions, solutions, capsules, creams, ointments, aerosols, and the like.

The compositions may include those compositions suitable for oral, rectal, topical, parenteral (including subcutaneous, intramuscular, intra-articular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, compositions may be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the compositions with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Soft gelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or soft gelatin capsules, for example, for identification or in order to characterize combinations of active compound doses, or to disguise the capsule contents for usage in clinical or other studies.

In some embodiments, compositions will typically be formulated in such vehicles at a concentration of about 0.1 mg/ml to 100 mg/ml.

For the prevention or treatment of disease, the appropriate dosage of the composition will depend on the type of disease to be treated, as defined above, the severity and course of the disease, whether the compositions are administered for preventive or therapeutic purposes, previous therapy, the patient's clinical history and response to the composition, and the discretion of the attending physician. The composition is suitably administered to the patient at one time or over a series of treatments.

According to another embodiment of the invention, the effectiveness of the composition in preventing or treating disease may be improved by administering the composition serially or in combination with another agent that is effective for those purposes such as, for example, alkylating agents, folic acid antagonists, anti-metabolites of nucleic acid metabolism, antibiotics, pyrimidine analogs, 5-fluorouracil, purine nucleosides, amines, amino acids, triazol nucleosides, corticosteroids, calcium, retinoids, lipoxygenase and cyclooxygenase inhibitors, fumaric acid and its salts, analgesics, psychopharmaceuticals, local anesthetics, spasmolytics, and beta-blockers. Such other agents may be present in the composition being administered or may be administered separately. The composition may be suitably administered serially or in combination with radiological treatments, whether involving irradiation or administration of radioactive substances.

In an embodiment, aptamers are used to treat pain, shock and inflammation by blocking oxidized linoleic acid metabolites. Aptamers may include nucleic acid aptamers or segments of aptamers (binding sites) that have a high affinity binding to 9-hydroxyoctadecadienoic acid (9-HODE) and/or 13-hydroxyoctadecadienoic acid (13-HODE). Aptamers that have a high affinity to 9-HODE and 13-HODE include, but are not limited to: 5'-ATA CGG GAG CCA ACA CCA CCG AAT GTG CTG CAG GAC TAA TCT GGA TGG CCA TGC AGA GCA GGT GTG ACG GAT-3' ("SEQ ID NO. 84") for 9-HODE; and 5'-ATC CGT CAC ACC TGC TCT GGG GGG GGA AGC TCG TGG TAT AAG GGG CGT TGA GGT GGT GTI GGC TCC CGT AT-3' ("SEQ ID NO. 67") for the OLAM 13-HODE.

Figure 2:
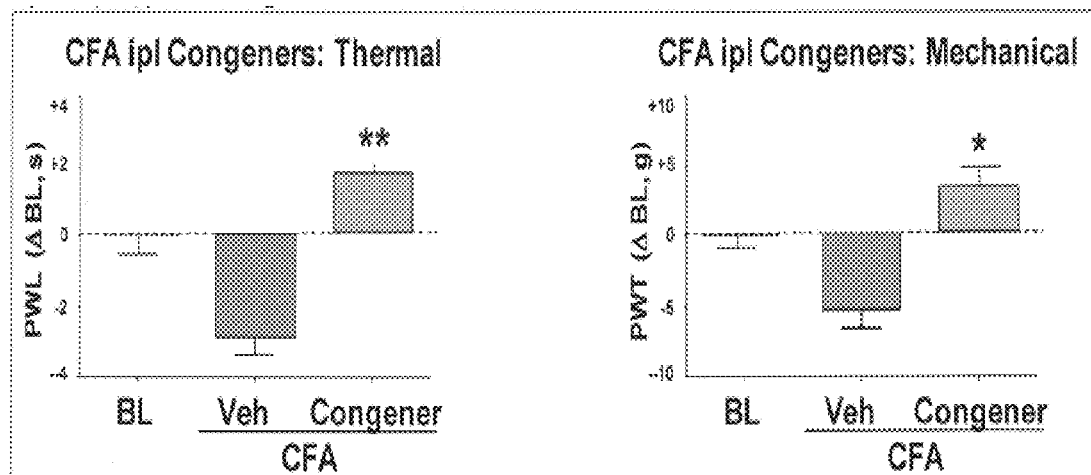
FIG. 2 depicts data which shows that injection of SEQ ID NO. 84 into rat hindpaws inflamed with complete Freund's adjuvant (CFA) produces a significant reduction in pain responses to both thermal and mechanical stimuli.

Preliminary data indicates that pre-treatment with SEQ ID NO. 84 (anti-9-HODE aptamer) blocks activation of cultured capsaicin-sensitive neurons using patch clamp electrophysiology (FIG. 1). Importantly SEQ ID NO. 84 does not block capsaicin itself indicating that the compound is selective against 9-HODE and does not block capsaicin or TRPV1 directly. FIG. 2 reveals that the local (hindpaw) injection of SEQ ID NO. 84 into rat hindpaws inflamed with complete Freund's adjuvant (CFA) produces a significant reduction in pain responses to both thermal and mechanical stimuli.

In some embodiments, the CYP-targeting and OLAM-targeting aptamers may be the full length aptamers as in SEQ ID NO. 84, SEQ ID NO. 67 or any of the CYP-targeting aptamer clones listed herein. In alternative embodiments, one or more segments or fragments of any of the aforementioned full-length aptamers are used. It is expected that aptamer segments of less than 25 nucleic acids, less than 20 nucleic acids, less than 15 nucleic acids, less than 10 nucleic acids and/or less than or equal to 5 nucleic acids in length comprise the active portion of the aptamer (i.e. the segment(s) or fragment(s) of the full-length aptamer originally identified that attaches to the OLAM binding site, and thus is/are primarily responsible for the outcome desired). It is desirable to minimize the absolute number of nucleic acids used. In general, the fewer the absolute number of nucleic acids used in two otherwise equally efficacious aptamers, the greater the likelihood the shorter aptamer will: 1.) be able to cross the blood-brain barrier; 2.) be able to move across the plasma membrane of cells and enter the cell cytoplasm, and; 3.) be more economical to manufacture.

In further embodiments, one or more segments or fragments comprising the active portions of two or more full-length aptamers may be bonded together (covalently or otherwise) yielding a multi-valent aptamer of the fewest absolute number of nucleic acids necessary to achieve the desired outcome. These shortened multi-valent aptamers may or may not be bound to a plasma protein binding compound.

Certain embodiments of the present invention include aptamers with nucleic acid sequences that are 80, 85, 90, 95, 98, or 100% identical to the sequence of SEQ ID NO. 84, SEQ ID NO. 67, any of the CYP-targeting aptamer clones listed beginning on page 11 or any active segment or fragment thereof.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A compound comprising an aptamer having the structure 5'-ATA CGG GAG CCA ACA CCA CCG AAT GTG CTG CAG GAC TAA TCT GGA TGG CCA TGC AGA GCA GGT GTG ACG GAT-3' (SEQ ID NO. 84).

2. The compound of claim 1, further comprising a compound that improves binding to plasma proteins, delivery to inflamed tissue and/or exerts intrinsic pharmacodynamic properties coupled to the aptamer (SEQ ID NO. 84).

3. The compound of claim 1, further comprising a nonsteroidal anti-inflammatory drug coupled to the aptamer (SEQ ID NO. 84).

4. The compound of claim 1, further comprising a steroid coupled to the aptamer (SEQ ID NO. 84).

5. The compound of claim 1, further comprising an antihistamine coupled to the aptamer (SEQ ID NO. 84).

6. The compound of claim 1, further comprising a polyethylene glycol coupled to the aptamer (SEQ ID NO. 84).

7. A compound comprising an aptamer having the structure 5'-ATC CGT CAC ACC TGC TCT GGG GGG GGA AGC

TCG TGG TAT AAG GGG CGT TGA GGT GGT GTT GGC TCC CGT AT-3' (SEQ ID NO. 67).

8. The compound of claim 7, further comprising a compound that improves binding to plasma proteins, delivery to inflamed tissue and/or exerts intrinsic pharmacodynamic properties coupled to the aptamer (SEQ ID NO. 67).

9. The compound of claim 7, further comprising a nonsteroidal anti-inflammatory drug coupled to the aptamer (SEQ ID NO. 67).

10. The compound of claim 7, further comprising a steroid coupled to the aptamer (SEQ ID NO. 67).

11. The compound of claim 7, further comprising an antihistamine coupled to the aptamer (SEQ ID NO. 67).

12. The compound of claim 7, further comprising a polyethylene glycol coupled to the aptamer (SEQ ID NO. 67).

13. A compound comprising:
a first aptamer having the structure 5'-ATA CGG GAG CCA ACA CCA CCG AAT GTG CTG CAG GAC TAA TCT GGA TGG CCA TGC AGA GCA GGT GTG ACG GAT-3' (SEQ ID NO. 84) coupled to a second aptamer having the structure 5'-ATC CGT CAC ACC TGC TCT GGG GGG GGA AGC TCG TGG TAT AAG GGG CGT TGA GGT GGT GTT GGC TCC CGT AT-3' (SEQ ID NO. 67).

14. The compound of claim 13, further comprising a linker molecule coupling the first aptamer (SEQ ID NO. 84) to the second aptamer (SEQ ID NO. 67).

15. The compound of claim 13, further comprising a compound that improves binding to plasma proteins, delivery to inflamed tissue and/or exerts intrinsic pharmacodynamic properties coupled to the first aptamer (SEQ ID NO. 84) or the second aptamer (SEQ ID NO. 67).

16. The compound of claim 13, further comprising a nonsteroidal anti-inflammatory drug coupled to the first aptamer (SEQ ID NO. 84) or the second aptamer (SEQ ID NO. 67).

17. The compound of claim 13, further comprising a steroid coupled to the first aptamer (SEQ ID NO. 84) or the second aptamer (SEQ ID NO. 67).

18. The compound of claim 13, further comprising an antihistamine coupled to the first aptamer (SEQ ID NO. 84) or the second aptamer (SEQ ID NO. 67).

19. The compound of claim 13, further comprising a polyethylene glycol coupled to the first aptamer (SEQ ID NO. 84) or the second aptamer (SEQ ID NO. 67).

20. A method of assessing the level of pain in a subject comprising analyzing a bodily fluid sample from the subject with a diagnostic assay that uses a compound of claim 1 and/or a compound of claim 7.

21. The method of claim 20, wherein the diagnostic assay comprises lateral flow or chromatographic test strips, ELISA-like enzymatic microplate assays, electochemiluminescence (ECL), and fluorescence assays including standard intensity-based assays, lifetime or fluorescence decay assays, fluorescence resonance energy transfer (FRET) assays, fluorescence polarization or anisotropy assays.

22. The method of claim 20, wherein the bodily fluid sample comprises serum, sputum or saliva, urine, cerebrospinal fluid, or interstitial fluid.

* * * * *

SEQUENCE LISTING

```
<160> NUMBER OF SEQ ID NOS: 109

<210> SEQ ID NO 1
<211> LENGTH: 72
<212> TYPE: DNA
<213> ORGANISM: Artificial Sequence
<220> FEATURE:
<223> OTHER INFORMATION: Synthetic Sequence

<400> SEQUENCE: 1
atacgggagc caacaccatc atgctactac cgggcccttt catcctaagc acggagagca     60
ggtgtgacgg at                                                         72

<210> SEQ ID NO 2
<211> LENGTH: 72
<212> TYPE: DNA
<213> ORGANISM: Artificial Sequence
<220> FEATURE:
<223> OTHER INFORMATION: Synthetic sequence

<400> SEQUENCE: 2
atccgtcaca cctgctctcc gtgcttagga tgaaagggcc cggtagtagc atgatggtgt     60
tggctcccgt at                                                         72

<210> SEQ ID NO 3
<211> LENGTH: 72
<212> TYPE: DNA
<213> ORGANISM: Artificial Sequence
<220> FEATURE:
<223> OTHER INFORMATION: Synthetic sequence
```

<400> SEQUENCE: 3
atacgggagc caacaccatc caatgaggcc atggaccggt aaactcggac gcgcagagca    60
ggtgtgacgg at    72

<210> SEQ ID NO 4
<211> LENGTH: 72
<212> TYPE: DNA
<213> ORGANISM: Artificial Sequence
<220> FEATURE:
<223> OTHER INFORMATION: Synthetic sequence

<400> SEQUENCE: 4
atccgtcaca cctgctctgc gcgtccgagt ttaccggtcc atggcctcat tggatggtgt    60
tggctcccgt at    72

<210> SEQ ID NO 5
<211> LENGTH: 72
<212> TYPE: DNA
<213> ORGANISM: Artificial Sequence
<220> FEATURE:
<223> OTHER INFORMATION: Synthetic sequence

<400> SEQUENCE: 5
atacgggagc caacaccagt ccgttatgac atgtccggac ccgtacgcgt gtcaagagca    60
ggtgtgacgg at    72

<210> SEQ ID NO 6
<211> LENGTH: 72
<212> TYPE: DNA
<213> ORGANISM: Artificial Sequence
<220> FEATURE:
<223> OTHER INFORMATION: Synthetic sequence

<400> SEQUENCE: 6
atccgtcaca cctgctcttg acacgcgtac gggtccggac atgtcataac ggactggtgt    60
tggctcccgt at    72

<210> SEQ ID NO 7
<211> LENGTH: 72
<212> TYPE: DNA
<213> ORGANISM: Artificial Sequence
<220> FEATURE:
<223> OTHER INFORMATION: Synthetic sequence

<400> SEQUENCE: 7
atacgggagc caacaccatg cccgctgtag tggtctctta acttaccctc gtgcagagca    60
ggtgtgacgg at    72

<210> SEQ ID NO 8
<211> LENGTH: 72
<212> TYPE: DNA
<213> ORGANISM: Artificial Sequence
<220> FEATURE:
<223> OTHER INFORMATION: Synthetic sequence

<400> SEQUENCE: 8
atccgtcaca cctgctctgc acgagggtaa gttaagagac cactacagcg ggcatggtgt    60
tggctcccgt at    72

<210> SEQ ID NO 9
<211> LENGTH: 72

<212> TYPE: DNA
<213> ORGANISM: Artificial Sequence
<220> FEATURE:
<223> OTHER INFORMATION: Synthetic sequence

<400> SEQUENCE: 9
atacgggagc caacaccacc cccccatact cttatttgcg acctctttcg ctacagagca    60
ggtgtgacgg at                                                       72

<210> SEQ ID NO 10
<211> LENGTH: 72
<212> TYPE: DNA
<213> ORGANISM: Artificial Sequence
<220> FEATURE:
<223> OTHER INFORMATION: Synthetic sequence

<400> SEQUENCE: 10
atccgtcaca cctgctctgt agcgaaagag gtcgcaaata agagtatggg ggggtggtgt    60
tggctcccgt at                                                       72

<210> SEQ ID NO 11
<211> LENGTH: 72
<212> TYPE: DNA
<213> ORGANISM: Artificial Sequence
<220> FEATURE:
<223> OTHER INFORMATION: Synthetic sequence

<400> SEQUENCE: 11
atacgggagc caacaccatc tcacccatgc ccacaaccag tccacgctac gccgagagca    60
ggtgtgacgg at                                                       72

<210> SEQ ID NO 12
<211> LENGTH: 72
<212> TYPE: DNA
<213> ORGANISM: Artificial Sequence
<220> FEATURE:
<223> OTHER INFORMATION: Synthetic sequence

<400> SEQUENCE: 12
atccgtcaca cctgctctcg gcgtagcgtg gactggttgt gggcatgggt gagatggtgt    60
tggctcccgt at                                                       72

<210> SEQ ID NO 13
<211> LENGTH: 72
<212> TYPE: DNA
<213> ORGANISM: Artificial Sequence
<220> FEATURE:
<223> OTHER INFORMATION: Synthetic sequence

<400> SEQUENCE: 13
atacgggagc caacaccact tcattaagtg gtattttggg caggagagca tcacagagca    60
ggtgtgacgg at                                                       72

<210> SEQ ID NO 14
<211> LENGTH: 72
<212> TYPE: DNA
<213> ORGANISM: Artificial Sequence
<220> FEATURE:
<223> OTHER INFORMATION: Synthetic sequence

<400> SEQUENCE: 14
atccgtcaca cctgctctgt gatgctctcc tgcccaaaat accacttaat gaagtggtgt    60

-continued tggctcccgt at                                                              72

<210> SEQ ID NO 15
<211> LENGTH: 71
<212> TYPE: DNA
<213> ORGANISM: Artificial Sequence
<220> FEATURE:
<223> OTHER INFORMATION: Synthetic sequence

<400> SEQUENCE: 15
atacgggagc caacaccacc aggatacaac cccaccatag actattcact gatagagcag        60
gtgtgacgga t                                                              71

<210> SEQ ID NO 16
<211> LENGTH: 71
<212> TYPE: DNA
<213> ORGANISM: Artificial Sequence
<220> FEATURE:
<223> OTHER INFORMATION: Synthetic sequence

<400> SEQUENCE: 16
atccgtcaca cctgctctat cagtgaatag tctatggtgg ggttgtatcc tggtggtgtt        60
ggctcccgta t                                                              71

<210> SEQ ID NO 17
<211> LENGTH: 72
<212> TYPE: DNA
<213> ORGANISM: Artificial Sequence
<220> FEATURE:
<223> OTHER INFORMATION: Synthetic sequence

<400> SEQUENCE: 17
atacgggagc caacaccaag gcgcgcatta atttaatgac agagatcacg aatcagagca        60
ggtgtgacgg at                                                             72

<210> SEQ ID NO 18
<211> LENGTH: 72
<212> TYPE: DNA
<213> ORGANISM: Artificial Sequence
<220> FEATURE:
<223> OTHER INFORMATION: Synthetic sequence

<400> SEQUENCE: 18
atccgtcaca cctgctctga ttcgtgatct ctgtcattaa attaatgcgc gccttggtgt        60
tggctcccgt at                                                             72

<210> SEQ ID NO 19
<211> LENGTH: 71
<212> TYPE: DNA
<213> ORGANISM: Artificial Sequence
<220> FEATURE:
<223> OTHER INFORMATION: Synthetic sequence

<400> SEQUENCE: 19
tacgggagcc aacaccactt gttttgcctt gatattctcc tatattgccc aagagagcag        60
gtgtgacgga t                                                              71

<210> SEQ ID NO 20
<211> LENGTH: 71
<212> TYPE: DNA
<213> ORGANISM: Artificial Sequence
<220> FEATURE:
<223> OTHER INFORMATION: Synthetic sequence

<400> SEQUENCE: 20
atccgtcaca cctgctctct tgggcaatat aggagaatat caaggcaaaa caagtggtgt    60
tggctcccgt a    71

<210> SEQ ID NO 21
<211> LENGTH: 72
<212> TYPE: DNA
<213> ORGANISM: Artificial Sequence
<220> FEATURE:
<223> OTHER INFORMATION: Synthetic sequence

<400> SEQUENCE: 21
atacgggagc caacaccacg cggctccttt atttgccaga tttacatgaa aggtagagca    60
ggtgtgacgg at    72

<210> SEQ ID NO 22
<211> LENGTH: 72
<212> TYPE: DNA
<213> ORGANISM: Artificial Sequence
<220> FEATURE:
<223> OTHER INFORMATION: Synthetic sequence

<400> SEQUENCE: 22
atccgtcaca cctgctctac ctttcatgta aatctggcaa ataaaggagc cgcgtggtgt    60
tggctcccgt at    72

<210> SEQ ID NO 23
<211> LENGTH: 72
<212> TYPE: DNA
<213> ORGANISM: Artificial Sequence
<220> FEATURE:
<223> OTHER INFORMATION: Synthetic sequence

<400> SEQUENCE: 23
atacgggagc caacaccatc aatctatact cccggttcac taatgtactc aagcagagca    60
ggtgtgacgg at    72

<210> SEQ ID NO 24
<211> LENGTH: 72
<212> TYPE: DNA
<213> ORGANISM: Artificial Sequence
<220> FEATURE:
<223> OTHER INFORMATION: Synthetic sequence

<400> SEQUENCE: 24
atccgtcaca cctgctctgc ttgagtacat tagtgaaccg ggagtataga ttgatggtgt    60
tggctcccgt at    72

<210> SEQ ID NO 25
<211> LENGTH: 71
<212> TYPE: DNA
<213> ORGANISM: Artificial Sequence
<220> FEATURE:
<223> OTHER INFORMATION: Synthetic sequence

<400> SEQUENCE: 25
atacgggagc caacaccact cggatatccc ctttatcttt ccgattcgtg tcgagagcag    60
gtgtgacgga t    71

<210> SEQ ID NO 26

```
<211> LENGTH: 71
<212> TYPE: DNA
<213> ORGANISM: Artificial Sequence
<220> FEATURE:
<223> OTHER INFORMATION: Synthetic sequence

<400> SEQUENCE: 26
atccgtcaca cctgctctcg acacgaatcg gaaagataaa ggggatatcc gagtggtgtt      60
ggctcccgta t                                                          71

<210> SEQ ID NO 27
<211> LENGTH: 72
<212> TYPE: DNA
<213> ORGANISM: Artificial Sequence
<220> FEATURE:
<223> OTHER INFORMATION: Synthetic sequence

<400> SEQUENCE: 27
atacgggagc caacaccatg gggggtact taaattggta ggggttgtt cttgagagca       60 ggtgtgacgg at                                                         72

<210> SEQ ID NO 28
<211> LENGTH: 72
<212> TYPE: DNA
<213> ORGANISM: Artificial Sequence
<220> FEATURE:
<223> OTHER INFORMATION: Synthetic sequence

<400> SEQUENCE: 28
atccgtcaca cctgctctca agaacaaccc cctaccaatt taagtacccc cccatggtgt     60
tggctcccgt at                                                         72

<210> SEQ ID NO 29
<211> LENGTH: 72
<212> TYPE: DNA
<213> ORGANISM: Artificial Sequence
<220> FEATURE:
<223> OTHER INFORMATION: Synthetic sequence

<400> SEQUENCE: 29
atccgtcaca cctgctctca catccaccta gtggtcttga ggcctcgttc tgagtggtgt     60
tggctcccgt at                                                         72

<210> SEQ ID NO 30
<211> LENGTH: 72
<212> TYPE: DNA
<213> ORGANISM: Artificial Sequence
<220> FEATURE:
<223> OTHER INFORMATION: Synthetic sequence

<400> SEQUENCE: 30
atacgggagc caacaccact cagaacgagg cctcaagacc actaggtgga tgtgagagca    60
ggtgtgacgg at                                                         72

<210> SEQ ID NO 31
<211> LENGTH: 72
<212> TYPE: DNA
<213> ORGANISM: Artificial Sequence
<220> FEATURE:
<223> OTHER INFORMATION: Synthetic sequence

<400> SEQUENCE: 31
atacgggagc caacaccagt gaggactaac gggttaaata acatgctgag ctgtagagca    60
```
ggtgtgacgg at                                                               72

<210> SEQ ID NO 32
<211> LENGTH: 72
<212> TYPE: DNA
<213> ORGANISM: Artificial Sequence
<220> FEATURE:
<223> OTHER INFORMATION: Synthetic sequence

<400> SEQUENCE: 32
atccgtcaca cctgctctac agctcagcat gttatttaac ccgttagtcc tcactggtgt          60
tggctcccgt at                                                               72

<210> SEQ ID NO 33
<211> LENGTH: 72
<212> TYPE: DNA
<213> ORGANISM: Artificial Sequence
<220> FEATURE:
<223> OTHER INFORMATION: Synthetic sequence

<400> SEQUENCE: 33
atacgggagc caacaccatg ccattcaggt tgtcaccaat ccgcattcgc gaacagagca          60
ggtgtgacgg at                                                               72

<210> SEQ ID NO 34
<211> LENGTH: 72
<212> TYPE: DNA
<213> ORGANISM: Artificial Sequence
<220> FEATURE:
<223> OTHER INFORMATION: Synthetic sequence

<400> SEQUENCE: 34
atccgtcaca cctgctctgt tcgcgaatgc ggattggtga caacctgaat ggcatggtgt          60
tggctcccgt at                                                               72

<210> SEQ ID NO 35
<211> LENGTH: 72
<212> TYPE: DNA
<213> ORGANISM: Artificial Sequence
<220> FEATURE:
<223> OTHER INFORMATION: Synthetic sequence

<400> SEQUENCE: 35
atacgggagc caacaccatg agctcacttc tgcaccctct acttccgccc ctccagagca          60
ggtgtgacgg at                                                               72

<210> SEQ ID NO 36
<211> LENGTH: 72
<212> TYPE: DNA
<213> ORGANISM: Artificial Sequence
<220> FEATURE:
<223> OTHER INFORMATION: Synthetic sequence

<400> SEQUENCE: 36
atccgtcaca cctgctctgg aggggcggaa gtagagggtg cagaagtgag ctcatggtgt          60
tggctcccgt at                                                               72

<210> SEQ ID NO 37
<211> LENGTH: 72
<212> TYPE: DNA
<213> ORGANISM: Artificial Sequence
<220> FEATURE:

<223> OTHER INFORMATION: Synthetic sequence

<400> SEQUENCE: 37
atacgggagc caacaccagg gggagtaaga gagacagacg caggatattc gggcagagca    60
ggtgtgacgg at                                                        72

<210> SEQ ID NO 38
<211> LENGTH: 72
<212> TYPE: DNA
<213> ORGANISM: Artificial Sequence
<220> FEATURE:
<223> OTHER INFORMATION: Synthetic sequence

<400> SEQUENCE: 38
atccgtcaca cctgctctgc ccgaatatcc tgcgtctgtc tctcttactc ccctggtgt     60 tggctcccgt at                                                        72

<210> SEQ ID NO 39
<211> LENGTH: 72
<212> TYPE: DNA
<213> ORGANISM: Artificial Sequence
<220> FEATURE:
<223> OTHER INFORMATION: Synthetic sequence

<400> SEQUENCE: 39
atacgggagc caacaccacg ccgctgtaga tccagactgt aatgttccat cggtagagca    60
ggtgtgacgg at                                                        72

<210> SEQ ID NO 40
<211> LENGTH: 72
<212> TYPE: DNA
<213> ORGANISM: Artificial Sequence
<220> FEATURE:
<223> OTHER INFORMATION: Synthetic sequence

<400> SEQUENCE: 40
atccgtcaca cctgctctac cgatggaaca ttacagtctg gatctacagc ggcgtggtgt    60
tggctcccgt at                                                        72

<210> SEQ ID NO 41
<211> LENGTH: 72
<212> TYPE: DNA
<213> ORGANISM: Artificial Sequence
<220> FEATURE:
<223> OTHER INFORMATION: Synthetic sequence

<400> SEQUENCE: 41
atacgggagc caacaccact atttgcgttg cacattacct gacaacttaa ctggagagca    60
ggtgtgacgg at                                                        72

<210> SEQ ID NO 42
<211> LENGTH: 72
<212> TYPE: DNA
<213> ORGANISM: Artificial Sequence
<220> FEATURE:
<223> OTHER INFORMATION: Synthetic sequence

<400> SEQUENCE: 42
atccgtcaca cctgctctcc agttaagttg tcaggtaatg tgcaacgcaa atagtggtgt    60
tggctcccgt at                                                        72

```
<210> SEQ ID NO 43
<211> LENGTH: 72
<212> TYPE: DNA
<213> ORGANISM: Artificial Sequence
<220> FEATURE:
<223> OTHER INFORMATION: Synthetic sequence

<400> SEQUENCE: 43
atacgggagc caacaccaac aaacgattca atcaacgtcc cagaccatgg gttcagagca      60
ggtgtgacgg at                                                         72

<210> SEQ ID NO 44
<211> LENGTH: 72
<212> TYPE: DNA
<213> ORGANISM: Artificial Sequence
<220> FEATURE:
<223> OTHER INFORMATION: Synthetic sequence

<400> SEQUENCE: 44
atccgtcaca cctgctctga acccatggtc tgggacgttg attgaatcgt ttgttggtgt      60
tggctcccgt at                                                         72

<210> SEQ ID NO 45
<211> LENGTH: 72
<212> TYPE: DNA
<213> ORGANISM: Artificial Sequence
<220> FEATURE:
<223> OTHER INFORMATION: Synthetic sequence

<400> SEQUENCE: 45
atacgggagc caacaccaga acggatgggg cttatgatat aggtgagaac gggtagagca      60
ggtgtgacgg at                                                         72

<210> SEQ ID NO 46
<211> LENGTH: 72
<212> TYPE: DNA
<213> ORGANISM: Artificial Sequence
<220> FEATURE:
<223> OTHER INFORMATION: Synthetic sequence

<400> SEQUENCE: 46
atccgtcaca cctgctctac ccgttctcac ctatatcata agccccatcc gttctggtgt      60
tggctcccgt at                                                         72

<210> SEQ ID NO 47
<211> LENGTH: 72
<212> TYPE: DNA
<213> ORGANISM: Artificial Sequence
<220> FEATURE:
<223> OTHER INFORMATION: Synthetic sequence

<400> SEQUENCE: 47
atacgggagc caacaccagt gtcaacaaga tccaatttta gacaacagag caccagagca      60
ggtgtgacgg at                                                         72

<210> SEQ ID NO 48
<211> LENGTH: 72
<212> TYPE: DNA
<213> ORGANISM: Artificial Sequence
<220> FEATURE:
<223> OTHER INFORMATION: Synthetic sequence

<400> SEQUENCE: 48
```

```
atccgtcaca cctgctctgg tgctctgttg tctaaaattg gatcttgttg acactggtgt    60
tggctcccgt at                                                        72

<210> SEQ ID NO 49
<211> LENGTH: 72
<212> TYPE: DNA
<213> ORGANISM: Artificial Sequence
<220> FEATURE:
<223> OTHER INFORMATION: Synthetic sequence

<400> SEQUENCE: 49
atacgggagc caacaccacg ttaagaccgc gaaatggtgc cacaacgagt ttggagagca    60
ggtgtgacgg at                                                        72

<210> SEQ ID NO 50
<211> LENGTH: 72
<212> TYPE: DNA
<213> ORGANISM: Artificial Sequence
<220> FEATURE:
<223> OTHER INFORMATION: Synthetic sequence

<400> SEQUENCE: 50
atccgtcaca cctgctctcc aaactcgttg tggcaccatt tcgcggtctt aacgtggtgt    60
tggctcccgt at                                                        72

<210> SEQ ID NO 51
<211> LENGTH: 72
<212> TYPE: DNA
<213> ORGANISM: Artificial Sequence
<220> FEATURE:
<223> OTHER INFORMATION: Synthetic sequence

<400> SEQUENCE: 51
atacgggagc caacaccatg cctgtatgac gtgtttccta acttgttgat ccctagagca    60
ggtgtgacgg at                                                        72

<210> SEQ ID NO 52
<211> LENGTH: 72
<212> TYPE: DNA
<213> ORGANISM: Artificial Sequence
<220> FEATURE:
<223> OTHER INFORMATION: Synthetic sequence

<400> SEQUENCE: 52
atccgtcaca cctgctctag ggatcaacaa gttaggaaac acgtcataca ggcatggtgt    60
tggctcccgt at                                                        72

<210> SEQ ID NO 53
<211> LENGTH: 72
<212> TYPE: DNA
<213> ORGANISM: Artificial Sequence
<220> FEATURE:
<223> OTHER INFORMATION: Synthetic sequence

<400> SEQUENCE: 53
atacgggagc caacaccaca acaacattaa ctctattccc ataaatcatt atacagagca    60
ggtgtgacgg at                                                        72

<210> SEQ ID NO 54
<211> LENGTH: 72
<212> TYPE: DNA
<213> ORGANISM: Artificial Sequence
```

<220> FEATURE:
<223> OTHER INFORMATION: Synthetic sequence

<400> SEQUENCE: 54
atccgtcaca cctgctctgt ataatgattt atgggaatag agttaatgtt gttgtggtgt    60
tggctcccgt at    72

<210> SEQ ID NO 55
<211> LENGTH: 72
<212> TYPE: DNA
<213> ORGANISM: Artificial Sequence
<220> FEATURE:
<223> OTHER INFORMATION: Synthetic sequence

<400> SEQUENCE: 55
atacgggagc caacaccaca gatgcgtacc tccccaaagt cccgatcagt tgccagagca    60
ggtgtgacgg at    72

<210> SEQ ID NO 56
<211> LENGTH: 72
<212> TYPE: DNA
<213> ORGANISM: Artificial Sequence
<220> FEATURE:
<223> OTHER INFORMATION: Synthetic sequence

<400> SEQUENCE: 56
atacgggagc caacaccaca aagtttagcg ttatgcaact cccccttata ctcgagagca    60
ggtgtgacgg at    72

<210> SEQ ID NO 57
<211> LENGTH: 72
<212> TYPE: DNA
<213> ORGANISM: Artificial Sequence
<220> FEATURE:
<223> OTHER INFORMATION: Synthetic sequence

<400> SEQUENCE: 57
atccgtcaca cctgctctcg agtataaggg ggagttgcat aacgctaaac tttgtggtgt    60
tggctcccgt at    72

<210> SEQ ID NO 58
<211> LENGTH: 72
<212> TYPE: DNA
<213> ORGANISM: Artificial Sequence
<220> FEATURE:
<223> OTHER INFORMATION: Synthetic sequence

<400> SEQUENCE: 58
atacgggagc caacaccacc accgactacc cagaacccgt tcttcccacc atgcagagca    60
ggtgtgacgg at    72

<210> SEQ ID NO 59
<211> LENGTH: 72
<212> TYPE: DNA
<213> ORGANISM: Artificial Sequence
<220> FEATURE:
<223> OTHER INFORMATION: Synthetic sequence

<400> SEQUENCE: 59
atccgtcaca cctgctctgc atggtgggaa gaacgggttc tgggtagtcg gtggtggtgt    60
tggctcccgt at    72

<210> SEQ ID NO 60
<211> LENGTH: 72
<212> TYPE: DNA
<213> ORGANISM: Artificial Sequence
<220> FEATURE:
<223> OTHER INFORMATION: Synthetic sequence

<400> SEQUENCE: 60
atacgggagc caacaccaaa attaacaacg ctgaatttag atttgtactg ccgtagagca    60
ggtgtgacgg at    72

<210> SEQ ID NO 61
<211> LENGTH: 72
<212> TYPE: DNA
<213> ORGANISM: Artificial Sequence
<220> FEATURE:
<223> OTHER INFORMATION: Synthetic sequence

<400> SEQUENCE: 61
atccgtcaca cctgctctac ggcagtacaa atctaaattc agcgttgtta attttggtgt    60
tggctcccgt at    72

<210> SEQ ID NO 62
<211> LENGTH: 72
<212> TYPE: DNA
<213> ORGANISM: Artificial Sequence
<220> FEATURE:
<223> OTHER INFORMATION: Synthetic sequence

<400> SEQUENCE: 62
atacgggagc caacaccaca gcatggccgg ttaagttgag acgattgtac tttaagagca    60
ggtgtgacgg at    72

<210> SEQ ID NO 63
<211> LENGTH: 72
<212> TYPE: DNA
<213> ORGANISM: Artificial Sequence
<220> FEATURE:
<223> OTHER INFORMATION: Synthetic sequence

<400> SEQUENCE: 63
atccgtcaca cctgctctta aagtacaatc gtctcaactt aaccggccat gctgtggtgt    60
tggctcccgt at    72

<210> SEQ ID NO 64
<211> LENGTH: 72
<212> TYPE: DNA
<213> ORGANISM: Artificial Sequence
<220> FEATURE:
<223> OTHER INFORMATION: Synthetic sequence

<400> SEQUENCE: 64
atacgggagc caacaccagc gaagccaaaa ctggtcgggc cgacgggatt cgttagagca    60
ggtgtgacgg at    72

<210> SEQ ID NO 65
<211> LENGTH: 72
<212> TYPE: DNA
<213> ORGANISM: Artificial Sequence
<220> FEATURE:
<223> OTHER INFORMATION: Synthetic sequence

<400> SEQUENCE: 65

```
atccgtcaca cctgctctaa cgaatcccgt cggcccgacc agttttggct tcgctggtgt    60
tggctcccgt at                                                       72

<210> SEQ ID NO 66
<211> LENGTH: 71
<212> TYPE: DNA
<213> ORGANISM: Artificial Sequence
<220> FEATURE:
<223> OTHER INFORMATION: Synthetic sequence

<400> SEQUENCE: 66
atacgggagc caacaccacc tcaacgcccc ttataccacg agcttccccc cccagagcag    60
gtgtgacgga t                                                        71

<210> SEQ ID NO 67
<211> LENGTH: 71
<212> TYPE: DNA
<213> ORGANISM: Artificial Sequence
<220> FEATURE:
<223> OTHER INFORMATION: Synthetic sequence

<400> SEQUENCE: 67
atccgtcaca cctgctctgg gggggaagc tcgtggtata aggggcgttg aggtggtgtt    60
ggctcccgta t                                                        71

<210> SEQ ID NO 68
<211> LENGTH: 72
<212> TYPE: DNA
<213> ORGANISM: Artificial Sequence
<220> FEATURE:
<223> OTHER INFORMATION: Synthetic sequence

<400> SEQUENCE: 68
atacgggagc caacaccaca tccttatcag ccaagaactt atactgtcca gcctagagca    60
ggtgtgacgg at                                                       72

<210> SEQ ID NO 69
<211> LENGTH: 72
<212> TYPE: DNA
<213> ORGANISM: Artificial Sequence
<220> FEATURE:
<223> OTHER INFORMATION: Synthetic sequence

<400> SEQUENCE: 69
atccgtcaca cctgctctag gctggacagt ataagttctt ggctgataag gatgtggtgt    60
tggctcccgt at                                                       72

<210> SEQ ID NO 70
<211> LENGTH: 72
<212> TYPE: DNA
<213> ORGANISM: Artificial Sequence
<220> FEATURE:
<223> OTHER INFORMATION: Synthetic sequence

<400> SEQUENCE: 70
atacgggagc caacaccagc ccactgccac gatatatgcg caaccgctgt ccgcagagca    60
ggtgtgacgg at                                                       72

<210> SEQ ID NO 71
<211> LENGTH: 72
<212> TYPE: DNA
```

<213> ORGANISM: Artificial Sequence
<220> FEATURE:
<223> OTHER INFORMATION: Synthetic sequence

<400> SEQUENCE: 71

```
atccgtcaca cctgctctgc ggacagcggt tgcgcatata tcgtggcagt gggctggtgt    60
tggctcccgt at                                                        72
```

<210> SEQ ID NO 72
<211> LENGTH: 72
<212> TYPE: DNA
<213> ORGANISM: Artificial Sequence
<220> FEATURE:
<223> OTHER INFORMATION: Synthetic sequence

<400> SEQUENCE: 72

```
atacgggagc caacaccatt gcgattcggc agggcagggt cgtaaatcct acatagagca    60
ggtgtgacgg at                                                        72
```

<210> SEQ ID NO 73
<211> LENGTH: 72
<212> TYPE: DNA
<213> ORGANISM: Artificial Sequence
<220> FEATURE:
<223> OTHER INFORMATION: Synthetic sequence

<400> SEQUENCE: 73

```
atccgtcaca cctgctctat gtaggattta cgaccctgcc ctgccgaatc gcaatggtgt    60
tggctcccgt at                                                        72
```

<210> SEQ ID NO 74
<211> LENGTH: 72
<212> TYPE: DNA
<213> ORGANISM: Artificial Sequence
<220> FEATURE:
<223> OTHER INFORMATION: Synthetic sequence

<400> SEQUENCE: 74

```
atacgggagc caacaccaca ccagctactc gagcaccata tgagattcaa tggcagagca    60
ggtgtgacgg at                                                        72
```

<210> SEQ ID NO 75
<211> LENGTH: 72
<212> TYPE: DNA
<213> ORGANISM: Artificial Sequence
<220> FEATURE:
<223> OTHER INFORMATION: Synthetic sequence

<400> SEQUENCE: 75

```
atccgtcaca cctgctctgc cattgaatct catatggtgc tcgagtagct ggtgtggtgt    60
tggctcccgt at                                                        72
```

<210> SEQ ID NO 76
<211> LENGTH: 72
<212> TYPE: DNA
<213> ORGANISM: Artificial Sequence
<220> FEATURE:
<223> OTHER INFORMATION: Synthetic sequence

<400> SEQUENCE: 76

```
atacgggagc caacaccact tgtcccccat cagcaccatc tccatgctcc tggcagagca    60
ggtgtgacgg at                                                        72
```

<210> SEQ ID NO 77
<211> LENGTH: 72
<212> TYPE: DNA
<213> ORGANISM: Artificial Sequence
<220> FEATURE:
<223> OTHER INFORMATION: Synthetic sequence

<400> SEQUENCE: 77
atccgtcaca cctgctctgc caggagcatg gagatggtgc tgatgggga caagtggtgt    60 tggctcccgt at                                                       72

<210> SEQ ID NO 78
<211> LENGTH: 72
<212> TYPE: DNA
<213> ORGANISM: Artificial Sequence
<220> FEATURE:
<223> OTHER INFORMATION: Synthetic sequence

<400> SEQUENCE: 78
atacgggagc caacaccact ctccccgcga gtttacctgt aaacacaacg catcagagca    60
ggtgtgacgg at                                                       72

<210> SEQ ID NO 79
<211> LENGTH: 72
<212> TYPE: DNA
<213> ORGANISM: Artificial Sequence
<220> FEATURE:
<223> OTHER INFORMATION: Synthetic sequence

<400> SEQUENCE: 79
atccgtcaca cctgctctga tgcgttgtgt ttacaggtaa actcgcgggg agagtggtgt    60
tggctcccgt at                                                       72

<210> SEQ ID NO 80
<211> LENGTH: 72
<212> TYPE: DNA
<213> ORGANISM: Artificial Sequence
<220> FEATURE:
<223> OTHER INFORMATION: Synthetic sequence

<400> SEQUENCE: 80
atacgggagc caacaccatc caatgaggcc atggaccggt aaactcggac gcgcagagca    60
ggtgtgacgg at                                                       72

<210> SEQ ID NO 81
<211> LENGTH: 72
<212> TYPE: DNA
<213> ORGANISM: Artificial Sequence
<220> FEATURE:
<223> OTHER INFORMATION: Synthetic sequence

<400> SEQUENCE: 81
atccgtcaca cctgctctgc gcgtccgagt ttaccggtcc atggcctcat tgatggtgt     60 tggctcccgt at                                                       72

<210> SEQ ID NO 82
<211> LENGTH: 72
<212> TYPE: DNA
<213> ORGANISM: Artificial Sequence
<220> FEATURE:
<223> OTHER INFORMATION: Synthetic sequence

<400> SEQUENCE: 82
atacgggagc caacaccaca aagtttagcg ttatgcaact cccccttata ctcgagagca       60
ggtgtgacgg at                                                            72

<210> SEQ ID NO 83
<211> LENGTH: 72
<212> TYPE: DNA
<213> ORGANISM: Artificial Sequence
<220> FEATURE:
<223> OTHER INFORMATION: Synthetic sequence

<400> SEQUENCE: 83
atccgtcaca cctgctctcg agtataaggg ggagttgcat aacgctaaac tttgtggtgt       60
tggctcccgt at                                                            72

<210> SEQ ID NO 84
<211> LENGTH: 72
<212> TYPE: DNA
<213> ORGANISM: Artificial Sequence
<220> FEATURE:
<223> OTHER INFORMATION: Synthetic sequence

<400> SEQUENCE: 84
atacgggagc caacaccacc gaatgtgctg caggactaat ctggatggcc atgcagagca       60
ggtgtgacgg at                                                            72

<210> SEQ ID NO 85
<211> LENGTH: 72
<212> TYPE: DNA
<213> ORGANISM: Artificial Sequence
<220> FEATURE:
<223> OTHER INFORMATION: Synthetic sequence

<400> SEQUENCE: 85
atccgtcaca cctgctctgc atggccatcc agattagtcc tgcagcacat tcggtggtgt       60
tggctcccgt at                                                            72

<210> SEQ ID NO 86
<211> LENGTH: 72
<212> TYPE: DNA
<213> ORGANISM: Artificial Sequence
<220> FEATURE:
<223> OTHER INFORMATION: Synthetic sequence

<400> SEQUENCE: 86
atacgggagc caacaccacc gaatgtgctg caagactaat ctggatggcc atgcagagca       60
ggtgtgacgg at                                                            72

<210> SEQ ID NO 87
<211> LENGTH: 72
<212> TYPE: DNA
<213> ORGANISM: Artificial Sequence
<220> FEATURE:
<223> OTHER INFORMATION: Synthetic sequence

<400> SEQUENCE: 87
atccgtcaca cctgctctgc atggccatcc agattagtct tgcagcacat tcggtggtgt       60
tggctcccgt at                                                            72

<210> SEQ ID NO 88
<211> LENGTH: 72

```
<212> TYPE: DNA
<213> ORGANISM: Artificial Sequence
<220> FEATURE:
<223> OTHER INFORMATION: Synthetic sequence

<400> SEQUENCE: 88
atacgggagc caacaccacg tcaggacctc catcgcccgg gcccgccgcc gctgagagca    60
ggtgtgacgg at                                                       72

<210> SEQ ID NO 89
<211> LENGTH: 72
<212> TYPE: DNA
<213> ORGANISM: Artificial Sequence
<220> FEATURE:
<223> OTHER INFORMATION: Synthetic sequence

<400> SEQUENCE: 89
atccgtcaca cctgctctca gcggcggcgg gcccgggcga tggaggtcct gacgtggtgt    60
tggctcccgt at                                                       72

<210> SEQ ID NO 90
<211> LENGTH: 69
<212> TYPE: DNA
<213> ORGANISM: Artificial Sequence
<220> FEATURE:
<223> OTHER INFORMATION: Synthetic sequence

<400> SEQUENCE: 90
atacgggagc caacaccatg aagtgcggtg tcgctctaac tgacgtatga aagagcaggt    60
gtgacggat                                                           69

<210> SEQ ID NO 91
<211> LENGTH: 69
<212> TYPE: DNA
<213> ORGANISM: Artificial Sequence
<220> FEATURE:
<223> OTHER INFORMATION: Synthetic sequence

<400> SEQUENCE: 91
atccgtcaca cctgctcttt catacgtcag ttagagcgac accgcacttc atggtgttgg    60
ctcccgtat                                                           69

<210> SEQ ID NO 92
<211> LENGTH: 71
<212> TYPE: DNA
<213> ORGANISM: Artificial Sequence
<220> FEATURE:
<223> OTHER INFORMATION: Synthetic sequence

<400> SEQUENCE: 92
atacgggagc caacaccatg tcttagtccg atactaacgt gccccttgtc cccagagcag    60
gtgtgacgga t                                                        71

<210> SEQ ID NO 93
<211> LENGTH: 71
<212> TYPE: DNA
<213> ORGANISM: Artificial Sequence
<220> FEATURE:
<223> OTHER INFORMATION: Synthetic sequence

<400> SEQUENCE: 93
atccgtcaca cctgctctgg ggacaagggg cacgttagta tcggactaag acatggtgtt    60
```
ggctcccgta t                                                            71

<210> SEQ ID NO 94
<211> LENGTH: 72
<212> TYPE: DNA
<213> ORGANISM: Artificial Sequence
<220> FEATURE:
<223> OTHER INFORMATION: Synthetic sequence

<400> SEQUENCE: 94
atacgggagc caacaccaca aagtttagcg ttatgcaact cccccttata ctcgagagca      60
ggtgtgacgg at                                                           72

<210> SEQ ID NO 95
<211> LENGTH: 72
<212> TYPE: DNA
<213> ORGANISM: Artificial Sequence
<220> FEATURE:
<223> OTHER INFORMATION: Synthetic sequence

<400> SEQUENCE: 95
atccgtcaca cctgctctcg agtataaggg ggagttgcat aacgctaaac tttgtggtgt      60
tggctcccgt at                                                           72

<210> SEQ ID NO 96
<211> LENGTH: 72
<212> TYPE: DNA
<213> ORGANISM: Artificial Sequence
<220> FEATURE:
<223> OTHER INFORMATION: Synthetic sequence

<400> SEQUENCE: 96
atacgggagc caacaccacg taagtgaccc cgcggtcagc aattaacacc agggagagca      60
ggtgtgacgg at                                                           72

<210> SEQ ID NO 97
<211> LENGTH: 72
<212> TYPE: DNA
<213> ORGANISM: Artificial Sequence
<220> FEATURE:
<223> OTHER INFORMATION: Synthetic sequence

<400> SEQUENCE: 97
atccgtcaca cctgctctcc ctggtgttaa ttgctgaccg cggggtcact tacgtggtgt      60
tggctcccgt at                                                           72

<210> SEQ ID NO 98
<211> LENGTH: 72
<212> TYPE: DNA
<213> ORGANISM: Artificial Sequence
<220> FEATURE:
<223> OTHER INFORMATION: Synthetic sequence

<400> SEQUENCE: 98
atacgggagc caacaccacc gaatgtgctg caagactaat ctggatggcc atgcagagca      60
ggtgtgacgg at                                                           72

<210> SEQ ID NO 99
<211> LENGTH: 72
<212> TYPE: DNA
<213> ORGANISM: Artificial Sequence
<220> FEATURE:
<223> OTHER INFORMATION: Synthetic sequence

```
<400> SEQUENCE: 99
atccgtcaca cctgctctgc atggccatcc agattagtct tgcagcacat tcggtggtgt      60
tggctcccgt at                                                          72

<210> SEQ ID NO 100
<211> LENGTH: 72
<212> TYPE: DNA
<213> ORGANISM: Artificial Sequence
<220> FEATURE:
<223> OTHER INFORMATION: Synthetic sequence

<400> SEQUENCE: 100
atacgggagc caacaccact cacacgccta gcgtcacggt ccctccccac ccccagagca      60
ggtgtgacgg at                                                          72

<210> SEQ ID NO 101
<211> LENGTH: 72
<212> TYPE: DNA
<213> ORGANISM: Artificial Sequence
<220> FEATURE:
<223> OTHER INFORMATION: Synthetic sequence

<400> SEQUENCE: 101
atccgtcaca cctgctctgg gggtggggag ggaccgtgac gctaggcgtg tgagtggtgt      60
tggctcccgt at                                                          72

<210> SEQ ID NO 102
<211> LENGTH: 72
<212> TYPE: DNA
<213> ORGANISM: Artificial Sequence
<220> FEATURE:
<223> OTHER INFORMATION: Synthetic sequence

<400> SEQUENCE: 102
atacgggagc caacaccatg ttacatcaac tgcatgaaga cgaggaatgt gatgagagca      60
ggtgtgacgg at                                                          72

<210> SEQ ID NO 103
<211> LENGTH: 72
<212> TYPE: DNA
<213> ORGANISM: Artificial Sequence
<220> FEATURE:
<223> OTHER INFORMATION: Synthetic sequence

<400> SEQUENCE: 103
atccgtcaca cctgctctca tcacattcct cgtcttcatg cagttgatgt aacatggtgt      60
tggctcccgt at                                                          72

<210> SEQ ID NO 104
<211> LENGTH: 72
<212> TYPE: DNA
<213> ORGANISM: Artificial Sequence
<220> FEATURE:
<223> OTHER INFORMATION: Synthetic sequence

<400> SEQUENCE: 104
atacgggagc caacaccaat gtgatccgac gtacacaggc cgagcgcttc tagtagagca      60
ggtgtgacgg at                                                          72

<210> SEQ ID NO 105
```

```
<211> LENGTH: 71
<212> TYPE: DNA
<213> ORGANISM: Artificial Sequence
<220> FEATURE:
<223> OTHER INFORMATION: Synthetic sequence

<400> SEQUENCE: 105
atccgtcaca cctgctctac tagaagcgct cggcctgtga cgtcggatca cattggtgtt    60
ggctcccgta t                                                         71

<210> SEQ ID NO 106
<211> LENGTH: 37
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (19)..(19)
<223> OTHER INFORMATION: n is a, c, g, or t

<400> SEQUENCE: 106
atccgtcaca cctgctctnt ggtgttggct cccgtat                             37

<210> SEQ ID NO 107
<211> LENGTH: 18
<212> TYPE: DNA
<213> ORGANISM: Artificial Sequence
<220> FEATURE:
<223> OTHER INFORMATION: Synthetic sequence

<400> SEQUENCE: 107
atacgggagc caacacca                                                  18

<210> SEQ ID NO 108
<211> LENGTH: 18
<212> TYPE: DNA
<213> ORGANISM: Artificial Sequence
<220> FEATURE:
<223> OTHER INFORMATION: Synthetic sequence

<400> SEQUENCE: 108
atccgtcaca cctgctct                                                  18

<210> SEQ ID NO 109
<211> LENGTH: 72
<212> TYPE: DNA
<213> ORGANISM: Artificial Sequence
<220> FEATURE:
<223> OTHER INFORMATION: Synthetic sequence

<400> SEQUENCE: 109
atccgtcaca cctgctctgg caactgatcg ggactttggg gaggtacgca tctgtggtgt    60
tggctcccgt at                                                        72
```